United States Patent [19]
Bhagwat et al.

[11] Patent Number: 5,665,721
[45] Date of Patent: Sep. 9, 1997

[54] HETEROCYCLIC SUBSTITUTED CYCLOPENTANE COMPOUNDS

[75] Inventors: Shripad S. Bhagwat, Libertyville; Marlon Daniel Cowart, Round Lake Beach, both of Ill.

[73] Assignee: Abbott Laboratories, Abbott Park, Ill.

[21] Appl. No.: 472,816

[22] Filed: Jun. 7, 1995

[51] Int. Cl.$^6$ ..................... A61K 31/505; C07D 407/02
[52] U.S. Cl. .................. 514/253; 514/258; 544/262; 544/280; 544/238
[58] Field of Search ................. 514/258, 253; 544/262, 280, 238

[56] References Cited

U.S. PATENT DOCUMENTS 3,296,261  1/1967  Partka et al. .................. 260/247.2

FOREIGN PATENT DOCUMENTS

| 0 496 617 A1 | 1/1992 | European Pat. Off. . |
| 521 463 | 6/1992 | European Pat. Off. . |
| 2574407 | 6/1986 | France . |
| WO 94/06438 | 3/1984 | WIPO . |
| WO 92/03452 | 3/1992 | WIPO . |
| WO 92/20822 | 11/1992 | WIPO . |
| WO 92/20823 | 11/1992 | WIPO . |
| 9413676 | 6/1994 | WIPO . |
| WO 94/17803 | 8/1994 | WIPO . |
| WO 94/18215 | 8/1994 | WIPO . |

OTHER PUBLICATIONS

Firestein et al., Protective effect of an Adenisine Kinase Inhibitor in Septic Shock, J. of Immunology, pp. 5853–5859, 1994.

Sawynok et al., The Role of Purines in Nociception, Neuroscience, vol. 32, No. 3, pp. 557–569, 1989.

Wolfe, et al., 4'–Modified Analogues of Aristeromycin and Neplanocin A: Synthesis and Inhibitory Activity Toward S–Adenosyl–L–Homocysteine Hydrolase, J. Med. Chen 1992, vol. 35, pp. 1782–1791.

Siddiqi, et al., Enantiospecific Synthesis of the Fluoro and Epimeric Derivatives of 5' Noraristeromycin, J. Chem. Soc., Chem. Commun., 1993, pp. 708–709.

Siddiqi, et al., Enantiospecific Synthesis of 5'-Noraristeromycin and Its 7–Deaza Derivative and A Formal Synthesis of (–)–5'–Homoaristeromycin, Nucleosides & Nucleotides, vol. 12(3&4), pp. 267–278 (1993).

Pudlo, et al., Synthesis and Antiviral Activity of Certain 4–and 4,5–Disubstituted 7–[2–Hydroxyethoxy)methyl]pyrrolo[2,3–d]pyrimidines, J. Med. Chem. 1988, vol. 31, No.11.

Miller, et al., Adenosine Kinase from Rabbit Liber, J. Bio. Chem. vol. 254, pp. 2346–2353, 1979.

Cottam, et al., New Adenosine Kinase Inhibitors with Oral Antiinflammatory Activity: Synthesis and Biological Evaluation, J. Med. Chem., 1993, vol. 36, No. 22, pp. 3424–3430.

Cottam, et al., New Adenosine Kinase Inhibitors with Oral Antiinflammatory Activity, Drugs of the Future, 1994, vol. 19(f); pp. 485–491.

Patel, et al., Synthesis and Antiviral Properties of (±)–5'–Noraristeromycin and Related Purine Carbocyclic Nucleosides. A New Lead for Anti–Human Cytomegalovirus Agent Design, J. Med. Chem. 1992, vol. 35, pp. 3372–3377.

Siddiqi et al., 3–Deaza–and 7–Deaza–5'–noraristeromycin and Their Antiviral Properties, J. Med. Chem., 38, 1035–1038, 1995.

Primary Examiner—Joseph K. McKane
Assistant Examiner—Richard S. Myers, Jr.
Attorney, Agent, or Firm—Monte R. Browder

[57] ABSTRACT

The present invention provides new heterocyclic substituted cyclopentane compounds that are useful in inhibiting adenosine kinase. The present invention also provides pharmaceutical compositions containing such compounds and methods of using such compounds for inhibiting adenosine kinase.

32 Claims, No Drawings

HETEROCYCLIC SUBSTITUTED CYCLOPENTANE COMPOUNDS

CROSS REFERENCE TO RELATED APPLICATIONS

This application is related to the following applications, which are incorporated herein by reference: U.S. patent application Ser. No. 08/480,019 entitled Adenosine Kinase Polynucleotides by Cowart, Halbert, Kerwin and McNally having Docket No. 5749.US.01 and U.S. patent application Ser. No. 08/479,614 entitled Adenosine Kinase Polypeptides by Cowart, Halbert, Kerwin and McNally having Docket No. 5749.US.D 1, all of which are filed concurrently with this application.

1. Technical Field

The present invention relates to new heterocyclic substituted cyclopentane compounds, which are useful in inhibiting adenosine kinase, to pharmaceutical compositions containing such compounds and to a method of using such compounds for inhibiting adenosine kinase.

2. Background of the Invention

Adenosine kinase (ATP:adenosine 5'-phosphotransferase, EC 2.7.1.20) is a ubiquitous enzyme which catalyzes the phosphorylation of adenosine to AMP, using ATP, preferentially, as the phosphate source. Magnesium is also required for the reaction, and the true cosubstrate is probably the MgATP$^{2-}$ complex (Palella et at., *J. Biol. Chem.* 1980, 255: 5264–5269). Adenosine kinase has broad tissue and species distribution, and has been isolated from yeast (Leibach et al., *Hoppe-Seyler's Z. Physiol. Chem.* 1971, 352: 328–344), a variety of mammalian sources (e.g. Miller et at., *J. Biol. Chem.* 1979, 254: 2339–2345; Palella et at., *J. Biol. Chem.* 1980, 255: 5264–5269; Yamada et al., *Comp. Biochem. Physiol.* 1982, 71B: 367–372; Rottlan and Miras-Portugal, *Eur. J. Biochem.,* 1985, 151: 365–371) and certain microorganisms (e.g. Lobelle-Rich and Reeves, *Am. J. Trop. Med. Hyg.* 1983, 32: 976–979; Datta et al., *J. Biol. Chem.* 1987, 262: 5515–5521). It has been found to be present in virtually every human tissue assayed including kidney, liver, brain, spleen, placenta and pancreas (Andres and Fox, *J. Biol. Chem.* 1979, 254: 11388–11393).

Adenosine kinase is a key enzyme in the control of the cellular concentrations of adenosine (Arch and Newsholme, *Essays Biochem.* 1978, 14: 82–123). Adenosine is a purine nucleoside that is an intermediate in the pathways of purine nucleotide degradation and salvage. In addition, adenosine has many important physiologic effects, many of which are mediated through the activation of specific ectocellular receptors, termed $P_1$ receptors (Burnstock, in *Cell Membrane Receptors for Drugs and Hormones,* 1978, (Bolis and Straub, eds) Raven, New York, pp. 107–118; Fredholm et al., *Pharmacol. Rev.* 1994, 46: 143–156). In the central nervous system, adenosine inhibits the release of certain neurotransmitters (Corradetti et al., *Eur. J. Pharmacol.* 1984, 104: 19–26), stabilizes membrane potential (Rudolphi et al., *Cerebrovasc. Brain Metab. Rev.* 1992, 4: 346–360), functions as an endogenous anticonvulsant (Dragunow, *Trends Pharmacol. Sci.* 1986, 7: 128–130) and may have a role as an endogenous neuroprotective agent (Rudolphi et al., *Trends Pharmacol. Sci.* 1992, 13: 439–445). Adenosine has also been implicated in modulating transmission in pain pathways in the spinal cord (Sawynok et al., Br. *J. Pharmacol.* 1986, 88: 923–930), and in mediating the analgesic effects of morphine (Sweeney et al., *J. Pharmacol. Exp. Ther.* 1987, 243: 657–665). In the immune system, adenosine inhibits certain neutrophil functions and exhibits anti-inflammatory effects (Cronstein, *J. Appl. Physiol.* 1994, 76: 5–13). Adenosine also exerts a variety of effects on the cardiovascular system, including vasodilation, impairment of atrioventricular conduction and endogenous cardioprotection in myocardial ischemia and reperfusion (Mullane and Williams, in *Adenosine and Adenosine Receptors* 1990 (Williams, ed) Humana Press, New Jersey, pp. 289–334). The widespread actions of adenosine also include effects on the renal, respiratory, gastrointestinal and reproductive systems, as well as on blood cells and adipocytes.

Endogenous adenosine release appears to have a role as a natural defense mechanism in various pathophysiologic conditions, including cerebral and myocardial ischemia, seizures, pain, inflammation and sepsis. While adenosine is normally present at low levels in the extracellular space, its release is locally enhanced at the site(s) of excessive cellular activity, trauma or metabolic stress. Once in the extracellular space, adenosine activates specific extracellular receptors to elicit a variety of responses which tend to restore cellular function towards normal (Bruns, *Nucleosides Nucleotides,* 1991, 10: 931–943; Miller and Hsu, *J. Neurotrauma,* 1992, 9: S563–S577). Adenosine has a half-life measured in seconds in extracellular fluids (Moser et al., *Am. J. Physiol.* 1989, 25: C799–C806), and its endogenous actions are therefore highly localized.

The inhibition of adenosine kinase can result in augmentation of the local adenosine concentrations at foci of tissue injury, further enhancing cytoprotection. This effect is likely to be most pronounced at tissue sites where trauma results in increased adenosine production, thereby minimizing systemic toxicities. Pharmacologic compounds directed towards adenosine kinase inhibition provide potentially effective new therapies for disorders benefited by the site- and event-specific potentiation of adenosine.

A number of compounds have been reported to inhibit adenosine kinase. The most potent of these include 5'-amino, 5'-deoxyadenosine (Miller et at., *J. Biol. Chem.* 1979, 254: 2339–2345), 5-iodotubercidin (Wotring and Townsend, *Cancer Res.* 1979, 39: 3018–3023) and 5'-deoxy-5-iodotubercidin (Davies et at., *Biochem. Pharmacol.* 1984, 33: 347–355).

Adenosine kinase is also responsible for the activation of many pharmacologically active nucleosides (Miller et al., *J. Biol. Chem.* 1979, 254: 2339–2345), including tubercidin, formycin, ribavirin, pyrazofurin and 6-(methylmercapto) purine riboside. These purine nucleoside analogs represent an important group of antimetabolites which possess cytotoxic, anticancer and antiviral properties. They serve as substrates for adenosine kinase and are phosphorylated by the enzyme to generate the active form. The loss of adenosine kinase activity has been implicated as a mechanism of cellular resistance to the pharmacological effects of these nucleoside analogs (e.g. Bennett et at., *Mol. Pharmacol.,* 1966, 2: 432–443; Caldwell et at., *Can. J. Biochem.,* 1967, 45: 735–744; Suttle et at., *Europ. J. Cancer,* 1981, 17: 43–51). Decreased cellular levels of adenosine kinase have also been associated with resistance to the toxic effects of 2'-deoxyadenosine (Hershfield and Kredich, *Proc. Natl. Acad. Sci. USA,* 1980, 77: 4292–4296). The accumulation of deoxyadenosine triphosphate (dATP), derived from the phosphorylation of 2'-deoxyadenosine, has been suggested as a toxic mechanism in the immune defect associated with inheritable adenosine deaminase deficiency (Kredich and Hershfield, in *The Metabolic Basis of Inherited Diseases,* 1989 (Scriver et at., eds), McGarw-Hill, New York, pp. 1045–1075).

BRIEF SUMMARY OF THE INVENTION

In one aspect, the present invention provides a heterocyclic substituted cyclopentane compound that acts as an adenosine kinase inhibitor. A compound of the present invention is a compound of the Formula I, below:

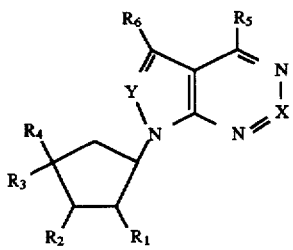

Formula I wherein

X is —N or —CR$_7$ where R$_7$ is hydrogen, halogen, loweralkyl, loweralkoxy or —S-loweralkyl;

Y is —N or —CH;

R$_1$ and R$_2$ are each independently hydrogen, hydroxy, alkoxy, or acyloxy or R$_1$ and R$_2$ are both hydroxy protected with an individual hydroxy protecting group or with a single dihydroxy-protecting group or R$_1$ and R$_2$ are absent and there is a double bond between the carbon atoms to which R$_1$ and R$_2$ are attached;

R$_3$ is hydrogen, hydroxy, loweralkyl or alkoxy;

R$_4$ is a) hydrogen, b) amino, c) halogen, d) hydroxy, e) sufonamido, f) —P(O)(OH)$_2$, g) —P(O)—R$_8$R$_9$ wherein R$_8$ and R$_9$ are each independently hydrogen, hydroxy, loweralkyl, aryl, or arylalkyl, h) —NHR$_{10}$ wherein R$_{10}$ is hydrogen or an amino protecting group, i) —NHC(O)NHR$_{11}$ where R$_{11}$ is hydrogen or loweralkyl, j) —AR$_{12}$ wherein A is O, S(O)$_n$ or —N(R$_{13}$)— wherein R$_{13}$ is hydrogen or loweralkyl, n is zero, one or two, and R$_{12}$ is hydrogen, loweralkyl, alkylsulfonyl, acyl, alkoxycarbonyl, aryl, arylalkyl, heteroaryl, arylsulfonyl, haloalkyl, heteroarylalkyl, heteroarylsulfonyl, aminoalkyl or heterocyclic, or k) P$_4$ is a nitrogen atom of a heteroaryl or heterocyclic ring; or R$_3$ and R$_4$ taken together are =O, or taken together with the carbon atom to which they are attached form a spirocyclic ring;

R$_5$ is hydrogen, loweralkyl, aryl, arylalkyl, heteroaryl, amino, alkylamino, alkoxy, acylamino, arylalkenyl, arylalkynyl, arylamino, arylmercapto, halogen, heterocyclic, hydrazino, thioalkoxy, —NHC(O)NH$_2$, or —NR$_{14}$R$_{15}$ wherein R$_{14}$ and R$_{15}$ are each independently hydrogen or an amino protecting group or —NR$_{14}$R$_{15}$ is a nitrogen containing heterocycle of 5 to 7 members; and R$_6$ is loweralkyl, cycloalkyl, alkenyl, alkynyl, alkoxy, alkoxycarbonyl, carboxy, aryl, heteroaryl, heteroarylalkyl, arylalkyl, arylalkenyl, arylalkynyl, heterocyclicalkyl, heterocyclicalkyl, heterocyclicalkynyl, cyano, halogen, heteroarylalkynyl, or —C(O)NHR$_{16}$ wherein R$_{16}$ is alkyl, aryl, or heterocyclic.

In a preferred embodiment, X and Y are both —CH, R$_1$ and R$_2$ are —OH; R$_3$ is hydrogen: R$_4$ is amino, hydroxyl, —NHR$_{10}$ or —NR$_{12}$R$_{13}$ where R$_{10}$, R$_{12}$ and R$_{13}$ are as defined in claim 1, R$_5$ is amino, arylalkyl, arylalkynyl, arylamino or halogen and R$_6$ is aryl, arylalkyl, arylalkenyl, arylalkynyl, or halogen. More preferably, R$_4$ is amino, methylamino, dimethylamino, carbamate, acylamino or heteroarylacylamino; R$_5$ is chloro, amino, phenylamino or 2-phenylethynyl; and R$_6$ is chloro, iodo, phenyl, 2-phenylethyl or 2-phenylethynyl.

In a more preferred embodiment, a compound of the present invention is a compound of Formula II, or IV below:

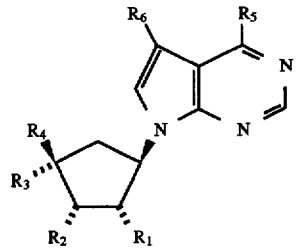

Formula II

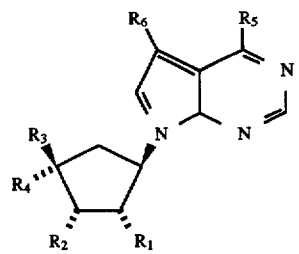

Formula IV where R$_1$, R$_2$, R$_3$, R$_4$, R$_5$ and R$_6$ are as defined above.

An especially preferred compound of the present invention has the Formula III or V below:

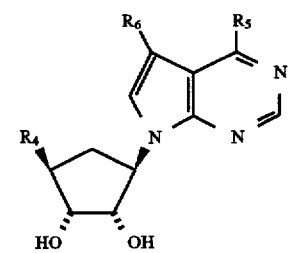

Formula III

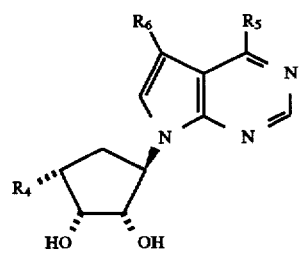

Formula V where R$_4$, R$_5$ and R$_6$ are as defined above. Preferred values of R$_4$, R$_5$ and R$_6$ are the same as set forth above. Exemplary and preferred compounds having the Formula I, II, or III are:

N7-((1'R,2'S,3'R,4'S)-2',3',4'-trihydroxycyclopentyl)-4,5-dichloro-pyrrolopyrimidine, N7-((1'R,2'S,3'R,4'S)-2',3',4'-trihydroxycyclopentyl)-4-chloro-5-iodo-pyrrolopyrimidine, N7-((1'R,2'S,3'R,4'S)-2',3',4'-trihydroxycyclopentyl)-4-amino-5-iodo-pyrrolopyrimidine, N7-((1'R,2'S,3'R,4'S)-2',3',4'-trihydroxycyclopentyl)-4-(phenyl)amino-5-iodo-pyrrolopyrimidine, N7-((1'R,2'S,3'R,4'S)-2',3',4'-trihydroxycyclopentyl)-4-chloro-5-phenyl-pyrrolopyrimidine, N7-((1'R,2'S,3'R,4'S)-2',3',4'-trihydroxycyclopentyl)-4-amino-5-phenyl-pyrrolopyrimidine, N7-((1'R,2'S,3'R,4'S)-2',3',4'-trihydroxycyclopentyl)-4-(phenyl)amino-5-phenyl-pyrrolopyrimidine, N7-((1'R,2'S,3'R,4'S)-2',3',4'-trihydroxycyclopentyl)-4,5-bis-phenylacetylenyl-pyrrolopyrimidine, N7-((1'R,2'S,3'R,4'S)-2',3',4'-trihydroxycyclopentyl)-4-chloro-5-phenylacetylenyl-pyrrolopyrimidine, N7-((1'R,2'S,3'R,4'S)-2',3',4'-trihydroxycyclopentyl)-4-amino-5-phenylacetylenyl-pyrrolopyrimidine, N7-((1'R,2'S,3'R,4'S)-2',3',4'-trihydroxycyclopentyl)-4-amino-5-((2phenyl)ethyl)-pyrrolopyrimidine, N7-((1'R,2'S,3'R,4'S)-2',3'-dihydroxy-4'-amino-cyclopentyl)-4-chloro-5-iodo-pyrrolopyrimidine, N7-((1'R,2'S,3'R,4'S)-2',3'-dihydroxy-4'-amino-cyclopentyl)-4-amino-5-iodo-pyrrolopyrimidine, N7-((1'R,2'S,3'R,4'S)-2',3'-dihydroxy-4'-(bis-t-butoxycarbonylamino)-cyclopentyl)-4-chloro-5-iodo pyrrolopyrimidine, N7-((1'R,2'S,3'R,4'S)-2',3'-dihydroxy-4'-(t-butoxycarbonylamino)-cyclopentyl)-4-amino-5-iodo-pyrrolopyrimidine, N7-((1'R,2'S,3'R,4'S)-2',3'-dihydroxy-4'-(methyl)amino-cyclopentyl)-4-chloro-5-methyl-pyrrolopyrimidine, N7-((1'R,2'S,3'R,4'S)-2',3'-dihydroxy-4'-(dimethyl) amino-cyclopentyl)-4-chloro-5-iodo-pyrrolopyrimidine and N7-((1'R,4'S)-cis-4'-amino-2'-cyclopentenyl)-4-chloro-5-iodo-pyrrolopyrimidine, N7-((1'R,2'S,3'R,4'S)-2',3'-dihydroxy-4'-(3"-nicotinoyl) amino-cyclopentyl)-4-chloro-5-iodo-pyrrolopyrimidine and salts, amides or esters of the above-compounds. The meaning of salt, ester and amide is defined hereinafter.

In another aspect, the present invention provides a pharmaceutical composition comprising a compound of the present invention in combination with a pharmaceutically acceptable carrier. Preferred compounds are those set forth above that have the Formula I, II, III, IV or V. A compound is present in a therapeutically effective amount.

In another aspect, the present invention provides a method of inhibiting adenosine kinase comprising exposing an adenosine kinase to an effective inhibiting amount of a compound of the present invention. Where the adenosine kinase is located in vivo, the compound is administered to the organism. Preferred compounds are the same as set forth above.

In another aspect, the present invention provides a method of treating cerebral ischemia, epilepsy, nociception, inflammation and sepsis in a patient in need of such treatment, comprising administering to the patient a therapeutically effective amount of a compound of the present invention.

DETAILED DESCRIPTION OF THE INVENTION

I. The Invention

The present invention relates to new heterocyclic substituted cyclopentane compounds which are useful in inhibiting adenosine kinase, to pharmaceutical compositions containing such compounds and to a method of using such compounds for inhibiting adenosine kinase.

II. Compounds

The compounds of the invention comprise asymmetrically substituted carbon atoms. As a result, all stereoisomers of the compounds of the invention are meant to be included in the invention, including racemic mixtures, mixtures of diastereomers, as well as single diastereomers of the compounds of the invention. The terms "S" and "R" configuration, as used herein, are as defined by the IUPAC 1974 Recommendations for Section E, Fundamental Stereochemistry, Pure Appl. Chem. (1976) 45, 13–30.

In one aspect, the present invention provides heterocyclic substitute cyclopentane compounds that are adenosine kinase inhibitors. An adenosine kinase inhibitor of the present invention is a compound of the Formula I, shown above.

In a more preferred embodiment, an adenosine kinase inhibitor of the present invention is a compound of Formula II or IV, shown above.

Exemplary hydroxy protecting groups are acetyl and methylethylidene.

Exemplary $R_4$ groups are acetoxy, acetylamino, t-butoxycarbonylamino, methoxycarbonylamino, nicotinoylamino, dimethylamino, trifluoroacetylamino, phthalimido, chloro- and dimethyl-amino,-pyridazinyl, pyridinylamino, pyridinyloxy, methylimidazolesulfonylamino, acetylmercapto, picolylmercapto, pyridinylmercapto, methyl- and aminoethyl-mercapto, diphenylphosphinyl, nicotinamide and imidazolyl.

Exemplary $R_5$ groups are halogen, amino, phenylamino, phenylacetylenyl, methoxy, and phenylmercapto.

Exemplary $R_6$ groups are halogen, phenyl, 2-phenylethyl, methyl, phenylacetylenyl, pyridinyl, carbomethoxy, carboxy, cyano, and cyclobutylcarboxamido.

Preferred compounds of the invention are compounds of Formula I, II or IV wherein X is —CH.

Other preferred compounds of the invention are compounds of Formula I, II or IV wherein $R_1$ and $R_2$ are —OH.

Other preferred compounds of the invention are compounds of Formula I, II or IV wherein $R_4$ is amino, hydroxyl, —$NHR_{10}$ or —$NR_{12}R_{13}$ where $R_{10}$, $R_{12}$, and $R_{13}$ are as defined above.

Other preferred compounds of the invention are compounds of Formula I, II or IV wherein $R_5$ is amino, arylalkyl, arylalkynyl, arylamino or halo.

Other preferred compounds of the invention are compounds of Formula I, II or IV wherein $R_6$ is aryl, arylalkyl, arylalkenyl, arylalkynyl, and halogen.

Other preferred compounds of the invention are compounds of Formula I, II or IV wherein X is —CH; $R_1$ and $R_2$ are —OH; $R_4$ is amino, hydroxyl, —$NHR_{10}$ or —$NR_{12}R_{13}$ where $R_{10}$, $R_{12}$ and $R_{13}$ are as defined above, $R_5$ is amino, arylalkyl, arylalkynyl, arylamino or halogen and $R_6$ is aryl, arylalkyl, arylalkenyl, arylalkynyl, or halogen.

Other preferred compounds of the invention are compounds of Formula I, II or IV wherein $R_3$ is hydrogen and $R_4$ is hydroxy, amino, or —$NHR_{10}$ wherein $R_{10}$ is hydrogen or an amino protecting group.

Other preferred compounds of the invention are compounds of Formula I, II or IV wherein $R_4$ is amino, methylamino, dimethylamino, carbamate, acylamino or heteroarylacylamino, $R_5$ is chloro, amino, phenylamino or 2-phenylethynyl; and $R_6$ is chloro, iodo, phenyl, 2-phenylethynyl or 2-phenylethyl.

More preferred compounds of the invention are compounds of Formula I, II or IV wherein X is CH; $R_1$ and $R_2$ are OH; $R_3$ is hydrogen; $R_4$ is amino, methylamino, dimethylamino, carbamate, acylamino or heteroarylacylamino; $R_5$ is chloro, amino, phenylamino or 2-phenylethynyl; and $R_6$ is chloro, iodo, phenyl, 2-phenylethyl or 2-phenylethynyl.

An especially preferred compound of the present invention has the Formula III or V, shown above.

Exemplary and preferred compounds having the Formula III or V are those wherein $R_4$ is hydroxyl and the values of $R_5$ and $R_6$ are: a) $R_5$ is Cl and $R_6$ is Cl, I, phenyl, or 2-phenylethynyl; b) $R_5$ is $NH_2$ and $R_6$ is I, phenyl, 2-phenylethyl or 2-phenylethynyl; c) $R_5$ is phenylamino and $R_6$ is I or phenyl; or d) $R_5$ is 2-phenylethynyl and $R_6$ is 2-phenylethynyl. Other exemplary and preferred compounds having the Formula III are those wherein a) $R_4$ is $NH_2$, $R_5$ is Cl or $NH_2$ and $R_6$ is I; b) $R_4$ is $Boc_2N$, $R_5$ is Cl and $R_6$ is I; c) $R_4$ is NHBoc, $R_5$ is $NH_2$ and $R_6$ is I; d) $R_4$ is $CH_3NH$, $R_5$ is Cl and $R_6$ is $CH_3$; e) $R_4$ is $(CH_3)_2N$, $R_5$ is Cl and $R_6$ is I; and f) $R_4$ is nicotinamide, $R_5$ is Cl and $R_6$ is I.

The present invention also contemplates salts, amides and esters of compounds having Formula I to V.

The term "acyl" as used herein refers to $R_{17}CO$—where $R_{17}$ is loweralkyl, heteroaryl or heterocyclic.

The term "acyloxy" as used herein refers to $R_{18}COO$— where $R_{18}$ is loweralkyl, heteroaryl or heterocyclic.

The term "alkanoylaminoalkyl" as used herein refers to —$NHC(O)R_{19}$ wherein $R_{19}$ is loweralkyl.

The term "alkanoyloxyalkyl" as used herein refers to —$OC(O)R_{20}$ wherein $R_{20}$ is loweralkyl.

The term "alkenyl" as used herein refers to branched or straight chain alkyl groups comprising 2 to 10 carbon atoms that has one or more carbon-carbon double bonds, including vinyl, propenyl, butenyl and the like.

The term "alkoxy" as used herein refers to $R_{21}O$ where $R_{21}$ is a loweralkyl or benzyl group. Representative alkoxy groups include methoxy, ethoxy, t-butoxy, benzyloxy and the like.

The term "alkoxycarbonyl" as used herein refers —$C(O)OR_{22}$ wherein $R_{22}$ is loweralkyl or cycloalkyl.

The term "alkoxycarbonyloxyalkyl" as used herein refers to —$OC(O)OR_{23}$ wherein $R_{23}$ is loweralkyl or cycloalkyl.

The term "alkoxycarbonylaminoalkyl" as used herein refers to —$NHC(O)OR_{24}$ wherein $R_{24}$ is loweralkyl.

The term "alkylamino" as used herein refers to $NHR_{25}$ where $R_{25}$ is a loweralkyl group.

The term "alkylmercapto" as used herein refers to $SHR_{26}$ where $R_{26}$ is a loweralkyl group.

The term "alkylsulfonyl" as used herein refers to $SO_2R_{27}$ where $R_{27}$ is a loweralkyl group.

The term "alkylaminocarbonylaminoalkyl" as used herein refers to —$NHC(O)NHR_{28}$ wherein $R_{28}$ is loweralkyl.

The term "alkynyl" as used herein refers to branched or straight chain alkyl groups comprising 2 to 10 carbon atoms that has one or more carbon-carbon triple bonds, including ethynyl, propynyl, butynyl and the like.

The term "aroyloxyalkyl" as used herein refers to a loweralkyl radical —$OC(O)R_{29}$ wherein $R_{29}$ is loweralkyl.

The term "aryl" as used herein refers to a phenyl or a $C_9$ or $C_{10}$ bicyclic carbocyclic ring system having one or more aromatic rings, including naphthyl, tetrahydronaphthyl, indanyl, indenyl and the like. The term "aryl" includes aryl groups that are unsubstituted or substituted with one or more substituents independently selected from loweralkyl, alkoxy, halo-substituted loweralkyl, cyano, thioalkoxy, alkoxycaronyl, hydroxy, halo, mercapto, nitro, amino, alkylamino, dialkylamino, carboxaldehyde, carboxy and carboxamide.

The terms "arylalkyl, arylalkenyl and arylalkynyl" as used herein refer to an aryl group appended to an alkyl, alkenyl or alkynyl group, respectively The term "arylamino" as used herein refers to an aryl group appended to an amino group.

The term "arylmercapto" as used herein refers to an aryl group appended to a mercapto (SH) group.

The term "dialkylamino" as used herein refers to —$NR_{30}R_{31}$ wherein $R_{30}$ and $R_{31}$ are independently selected from loweralkyl.

The term "halogen" or "halo" as used herein refers to Cl, Br, I and F.

The term "heteroaryl" as used herein refers to aryl in which one or more of the ring carbon atoms is replaced by a heterocyclic atom such as N, S, O or P.

The term "heteroarylalkyl" as used herein refers to a heteroaryl group appended to an alkyl group.

The term "heteroarylacylamino" as used herein refers to heteroarylC(O)NH—.

The term "heterocyclic group" or "heterocyclic" as used herein refers to any 3- or 4-membered ring containing a heteroatom selected from oxygen, nitrogen and sulfur, or a 5-, 6-, or 7-membered ring containing one, two or three nitrogen atoms; one nitrogen and one sulfur atom; or one nitrogen and one oxygen atom; wherein the 5-membered ring has 0–2 double bonds and the 6- or 7-membered ting has 0–3 double bonds; wherein the nitrogen and sulfur heteroatoms can optionally be oxidized; wherein the nitrogen heteroatom can optionally be quaternized; and, including any cyclic group in which any of the above heterocyclic rings is fused to a benzene ring or another 5-, 6- or 7-membered heterocyclic ring independently as defined above. Representative heterocyclics include indolyl, quinolyl, isoquinolyl, tetrahydroquinolyl, benzofuryl, benzothienylazetidinyl, pyrrolyl, pyrrolinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, benzimidazolyl, benzothiazolyl, benzoxazolyl, furyl, thienyl, trizolyl, benzothienyl, homopiperazinyl, homopiperidinyl, homomorpholinyl and the like.

The term "loweralkyl" as used herein refers to branched or straight chain, substituted or unsubstituted, alkyl groups comprising 1 to 10 carbon atoms including methyl, ethyl, propyl, isopropyl, butyl n-butyl, n-butyl, neopentyl and the like. A loweralkyl can be substituted with halo, mercapto, nitro, amino, and the like.

The term "thioalkoxy" or "mercaptoalkoxy" as used herein refers to —$SR_{16}$ wherein $R_{16}$ is a loweralkyl or benzyl group.

"Hydroxy-protecting group" or "O-protecting group" refers to a substituent which protects hydroxyl groups against undesirable reactions during synthetic procedures and includes, but is not limited to, substituted methyl ethers, for example, methoxymethyl, benzyloxymethyl, 2-methoxyethoxymethyl, 2-(trimethylsiyll)ethoxymethyl, ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in Greene, "Protective Groups In Organic Synthesis," (John Wiley & Sons, New York (1981), which is hereby incorporated by reference The term "N-protecting group" or "N-protected" as used herein refers to those groups intended to protect an amino group against undesirable reactions during synthetic procedures. Commonly used N-protecting groups are disclosed in Greene, "Protective Groups In Organic Synthesis," (John Wiley & Sons, New York (1981), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. Preferred N-protecting groups are formyl, acetyl, benzoyl, pivaloyl, phenylsulfonyl, benzyl, triphenylmethyl (trityl), t-butyloxycarbonyl (Boc), benzoyloxycarbonyl (Cbz) and the like.

Many of the terms as defined above include numerous groups (e.g., arylalkyl). It is to be understood that, in the context of the present invention, the last named group in such terms is the group that is appended to the cyclic structures (e.g., cyclopentane) of the Formulae I–V.

pharmaceutical Compositions

In a further aspect of the present invention pharmaceutical compositions are disclosed which comprise a compound of the present invention in combination with a pharmaceutically acceptable carrier.

The present invention includes one or more compounds, as set forth above, formulated into compositions together with one or more non-toxic physiologically tolerable or acceptable diluents, carriers, adjuvants or vehicles that are collectively referred to herein as diluents, for parenteral injection, for oral administration in solid or liquid form, for rectal or topical administration, or the like. As is well known the art, a compound of the present invention can exist in a variety of forms including pharmaceutically-acceptable salts, esters, amides and the like.

"Pharmaceutically-acceptable amide" refers to the pharmaceutically-acceptable, nontoxic amides of the compounds of the present invention which include amides formed with suitable organic acids or with amino acids, including short peptides consisting of from 1-to-6 amino acids joined by amide linkages which may be branched or linear, wherein the amino acids are selected independently from naturally-occurring amino acids, such as for example, glycine, alanine, leucine, valine, phenylalanine, proline, methionine, tryptophan, asparagine, aspartic acid, glutamic acid, glutamine, serine, threonine, lysine, arginine, tyrosine, histidine, ornithine, and the like.

"Pharmaceutically-acceptable ester" refers to the pharmaceutically-acceptable, nontoxic esters of the compounds of the present invention which include loweralkyl esters, wherein loweralkyl is as defined above, and C5–C7-cycloalkyl esters, wherein cycloalkyl refers to cyclic saturated hydrocarbon radicals, such as cyclopentyl, cyclohexyl, and the like. Also included are aryl-alkyl esters, wherein aryl and alkyl are as defined above. Representative examples include benzyl, phenethyl, and the like.

"Pharmaceutically-acceptable salts" refers to the pharmaceutically-acceptable, nontoxic, inorganic or organic acid addition salts of the compounds of the present invention, as described in greater detail below.

The compounds of the present invention can be used in the form of pharmaceutically-acceptable salts derived from inorganic or organic acids. These salts include, but are not limited to, the following: acetate, adipate, alginate, aspartate, benzoate, benzenesulfonate, bisulfate, butyrate, camphorate, camphorsulfonate, citrate, cyclopentanepropionate, digluconate, dodecylsulfate, ethanesulfonate, flavianate, fumarate, glucoheptonate, glycerophosphate, hemisulfate, heptonate, hexonoate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, phosphate, picrate, pivalate, propionate, succinate, tartrate, thiocyanate, tosylate, and undecanoate.

Appropriate cationic salts are also readily prepared by conventional procedures such as treating an acid of Formula I with an appropriate amount of base, such as an alkali or alkaline earth metal hydroxide, e.g., sodium, potassium, lithium, calcium, or magnesium, or an organic base such as an amine, e.g., dibenzylethylenediamine, cyclohexylamine, dicyclohexylamine, triethylamine, piperidine, pyrrolidine, benzylamine, and the like, or a quanternary ammonium hydroxide such as tetramethylammoninm hydroxide and the like. Also, the basic nitrogen-containing groups can be quaternized with such agents as loweralkyl halides, such as methyl, ethyl, propyl, and butyl chlorides, bromides, and iodides; dialkyl sulfates; long chain halides such as decyl, lauryl, myristyl, and stearyl chlorides, bromides and iodides; arylalkyl halides like benzyl and phenethyl bromides, and others. Water or oil-soluble or dispersible products are thereby obtained.

The salts of the present invention can be synthesized from the compounds of Formula I which contain a basic or acidic moiety by conventional methods, such as by reacting the free base or acid with stoichiometric amounts or with an excess of the desired salt forming inorganic acid or base in a suitable solvent or various combinations of solvents.

The compositions can be administered to humans and animals either orally, rectally, parenterally, intracisternally, intravaginally, intraperitoneally, locally, or as a buccal or nasal spray.

Compositions suitable for parenteral administration can comprise physiologically acceptable sterile aqueous or non-aqueous solutions, dispersions, suspensions or emulsions and sterile powders for reconstitution into such sterile solutions or dispersions. Examples of suitable diluents include water, ethanol, polyols, suitable mixtures thereof, vegetable oils and injectable organic esters such as ethyl oleate. Proper fluidity can be maintained, for example, by the use of a coating such as lecithin, by the maintenance of the required particle size in the case of dispersions and by the use of surfactants.

Compositions can also contain adjuvants such as preserving, wetting, emulsifying, and dispensing agents. Prevention of the action of microorganisms can be insured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form can be brought about by the use of agents delaying absorption, for example, aluminum monostearate and gelatin.

Besides such inert diluents, the composition can also include sweetening, flavoring and perfuming agents. Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixes of these substances, and the like.

IV. Process of Making Adenosine Kinase Inhibitor Compounds and Synthetic Intermediates Useful in such a process.

The present invention also relates to processes for preparing the compounds of Formula I–V and to the synthetic intermediates useful in such processes. Compounds of the present invention are prepared using standard synthetic procedures well known in the art The compounds of the present invention may be synthesized by methods illustrated in Schemes 1–10. In accordance with Scheme 1, certain heterocyclic bases and analogs are useful starting materials. Pyrrolopyrimidines 1 (A=Cl, B=H, Cl, Br, I, $CH_3$, CN)1have been described (L. B. Townsend, J. Meal. Chem. (1990) 33, 1984–1992; ibid, (1988) 31, 2086–2092; Tollman, J. Am. Chem. Soc. (1969) 91, 2102). Pyrazolopyrimidines 2 (A=$NH_2$, B=H, Br, I, CN, $CH_2CN$, Ph) have been described by (T. S. Leonora, V. G. Yashunskii; Khim. Geterotsiki. Soedin. (1982), 982–984;

E. C. Taylor, J. Org. Chem. (1966) 31, 34; Carboni, J. Am. Chem. Soc. (1958) 80, 2838; Kobayashi, Chem. Phar. Bull. (1973) 21, 941). 2-azapyrazolopyrimidines 4 (A=OH, NH₂, B=H) have been described (J. A. Montgomery, J. Med. Chem. (1975) 18, 564–567; ibid, (1972) 15, 182–189; R. K. Robins, J. Pharm. Sci. (1968) 57, 1044. While 2-azapyrrolopyrimidines 3 have not been described, they should be available from the corresponding pyrrolopyrimidines described in Scheme 2, using the method of Montgomery (J. Med. Chem. (1972) 15, 182–189) who used a four step method to convert substituted pyrazolopyrimidines 2 to 2-azapyrazolopyrimidines 4.

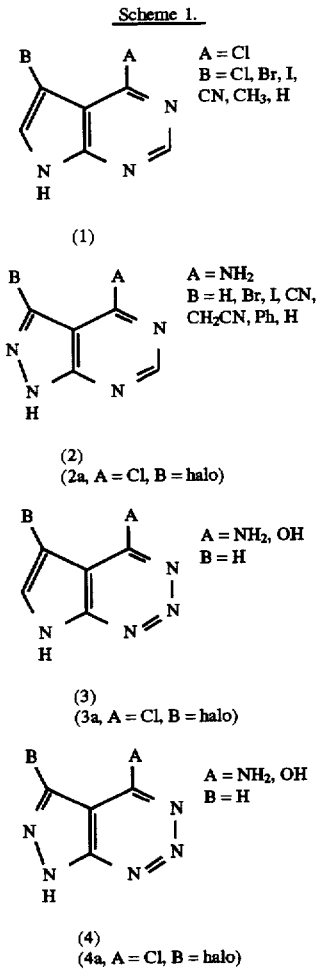

Where neccessary, the pyrrole nitrogen in the aforementioned heterocyclic bases 5 may be protected as for example the methoxymethyl ether 6 shown in Scheme 2 with methoxymethyl chloride and sodium hydride. The protecting group in 6 may be removed after synthetic transformation of the heterocyclic moiety by treatment with aqueous acid to give 5. Where synthetic intermediates 7 are required (either P=H or the protected form P=MOM), halogenation of unsubstituted (B=H) H) heterocycles may be effected by used of N-iodosuccinimide (NIS), N-bromosuccinimide (NBS), N-chlorosuccinimide (NCS,) or ICl as shown in Scheme 3 (Townsend, J. Med. Chem. (1988) 31, 2086–2092; Cocuzza, Tet. Lett. (1988) 29, 4061–4064).

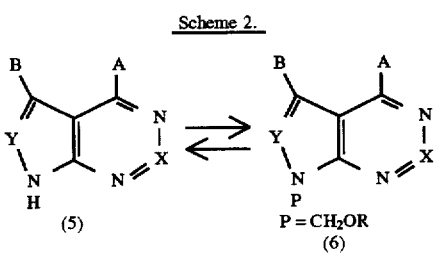

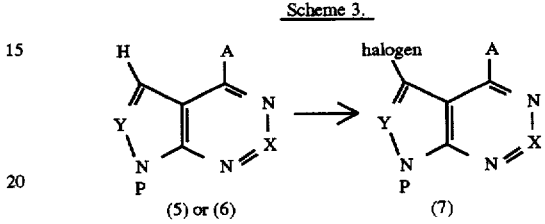

In the case where the heterocyclic base 8 (P=H or MOM) contains a substituent where A=NH₂, which is desired to be converted to a chlorine 9, the base may be diazotized by treatment with isoamyl nitrite, followed by treatment with hydrochloric acid to give A=Cl as shown in Scheme 4 (C. Overberger, Org. Syn. Coll. Vol. IV (1963) 182).

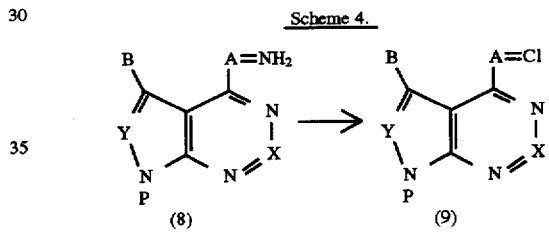

The Mitsunobu coupling of heterocyclic bases with substituted cyclopentenes like (1R,4S)-cis-4-hydroxy-2-cyclopentenyl acetate 10 (C. R. Johnson Tet. Lett. (1992) 33, 7287–7290) using triphenylphosphine and diethylazodicarboxylate to give 11 can be effected using known methods, as shown in Scheme 5 (Benner, Tet. Lett. (1991) 32, 7029–7032). The subsequently produced cyclopentenes may be deacetylated with ammonia to give alcohols 12. These may be treated with diethyl azodicarboxylate (DAST) to provide the allylic fluoride, which after treatment with osmium tetroxide provide 13 where R₃=F (Schneller, J. Chem. Soc., Chem. Comm. (1993) 708–709). The allylic alcohols may also be treated With nucleophiles containing acidic nitrogens (e.g., bis-t-butoxycarbonylamine, phthalimide), acidic oxygens (e.g., phenols), acidic sulfurs, (e.g., mercaptans, heteroaryl mercaptans), or phosphorus (e.g., dialkylphosphine oxides) in the presence of triphenylphosphine and diethylazodicarboxylate to give 13, using the Mitsunobu reaction. These products may in turn be treated with osmium tetroxide to give the corresponding diols 14. Alternately, the acetate 11 may be converted to 15 by treatment with nucleophiles containing acidic nitrogens (e.g., bis-t-butoxycarbonylamine, phthalimide), acidic oxygens (e.g., phenols), acidic sulfurs (e.g., mercaptans), or acidic phosphorus (e.g., dialkylphosphites) in the presence of base and tetra-kis(triphenylphosphine)palladium, or with free base amines in the presence of tetra-kis (triphenylphosphine)-palladium (Deardorff, J. Org. Chem.

(1989) 54, 2759–2762; Genet, Tet. Lett. (1983) 24, 2745–2748). These in turn can be treated with osmium tetroxide to give 16.

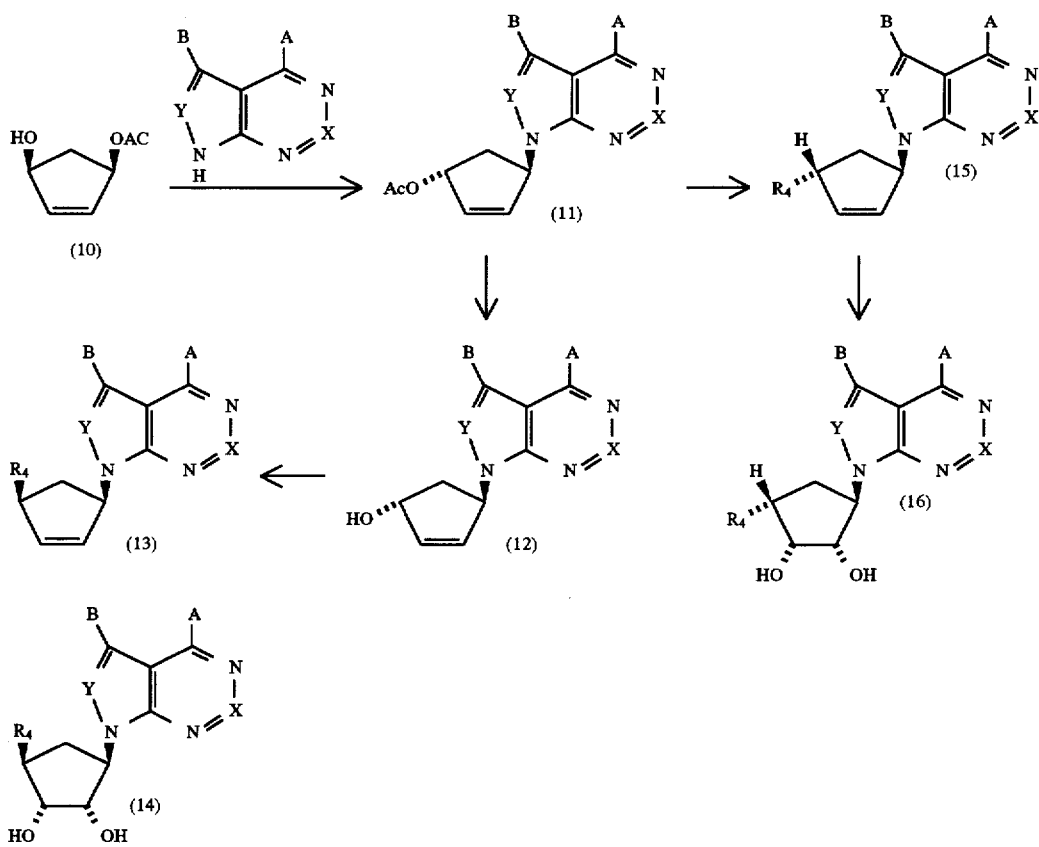

Scheme 5.

The halogenated heterocycles like 15 (B=I, Cl) can be converted to the alkylated, alkenylated, alkynylated or arylated derivatives (B=loweralkyl, aryl, heteroaryl, substituted alkynyl, substituted alkenyl) by treatment with an appropriate tributylstannyl (Stille coupling), organozinc (Negeshi modification of the Stille coupling), or sodium carbonate and an organoboronic acid (Suzuki reaction) derivative, in the presence of a catalytic amount of a palladium complex, like Pd(PPh$_3$)$_4$ or PdCl$_2$(PPh$_3$)$_2$.

The halogenated heterocycles like 15 can converted to cyanoheterocycles (B=CN) by treatment with copper (I) cyanide as shown in Scheme 6. Allkoxyheterocycles where B=O-alkyl can be produced by the action of sodium alkoxides on 15, catalyzed by copper salts like copper (I) iodide.

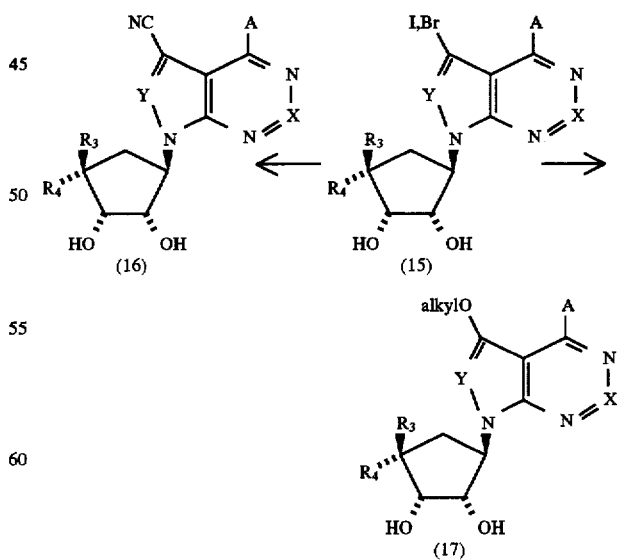

Scheme 6.

Additionally, the products of the invention can be produced by treating an allylic acetate 10 (or 10 protected with a TBS) (Greene & Wuts, in Protective Groups in Organic Synthesis, John Wiley and Sons, 199), with a heterocyclic base (1-5) and with a deprotonating agent such as lithium hydride, in the presence of tetrakis(triphenylphosphine) palladium (Benneche, Acta. Chem. Scan. (1992) 46, 761-771; Benneche, Tet. Lett. (1992) 33, 1085-1088). The resulting cyclopentenes 18 can be cis-hydroxylated with osmium tetroxide to provide 19, then treated with a fluoride source or acid to produce the trihydroxycyclopentanes 20. Alternatively, the hydroxyls can be protected as for example, the acetonide 21, produced by reaction with acetone in the presence of an acid catalyst. The acetonide 21, can then be deprotected with a fluoride source to give 21 (P'=H), and this treated with DAST, to give the fluoride 22 ($R_4$=F), or deoxygenated using the Barton reaction by formation of the xanthate ester, followed by treatment with tributyltin hydride and 1,1'-azobis(isobutyronitrile) (AIBN) to give 22 ($R_4$=H). The acetonide 21 (P'=H) can be oxided to the ketone 23 with DMSO/oxalyl chloride/Hunig's base (Swern reaction), which can then be treated with aqueous acid to give compounds where $R_3$=$R_4$=O. Alternately, the protected ketones 23 can be reacted with nucleophiles like alkyl or aryl lithium reagents or L-selectride to provide alcohols 24 ($R_3$=H, loweralkyl). These alchohols can then be treated with nucleophiles containing acidic nitrogens (bis-t-butoxycarbonylamine, phthalamide), acidic oxygens (phenols), acidic sulfurs (mercaptans), or phosphorus (dialkylphosphites) in the presence of triphenylphosphine and diethylazodicarboxylate to give 25 using the Mitsunobu reaction as described above, then deprotected to provide compounds of the invention 25 (where $R_4$=H, loweralkyl, $R_3$=N, O, S). Alternatively, the alcohols 24 can be converted to the methanesulfonates 26, which can be displaced with nucleophiles containing acidic nitrogens (bis-t-butoxycarbonylamine, phthalamide), acidic oxygens (phenols), acidic sulfurs (hydrogen sulfide or substituted mercaptans), or phosphorus (dialkylphosphites) in the presence of a base like potassium carbonate, or with compounds containing nucleophilic heteroatoms (for example, hydrazine) to provide 25 (after treatment with aqueous acid). The methanesulfonates 26 can also be displaced with amines in the free base form (methylamine, aniline, imidazole) to provide 25 (after treatment with aqueous acid).

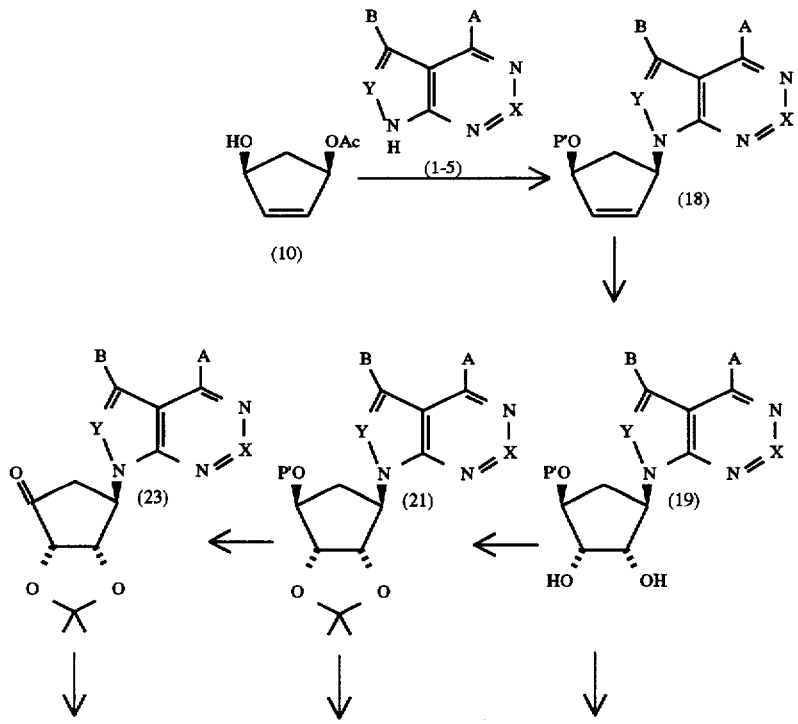

Scheme 7.

-continued
Scheme 7.

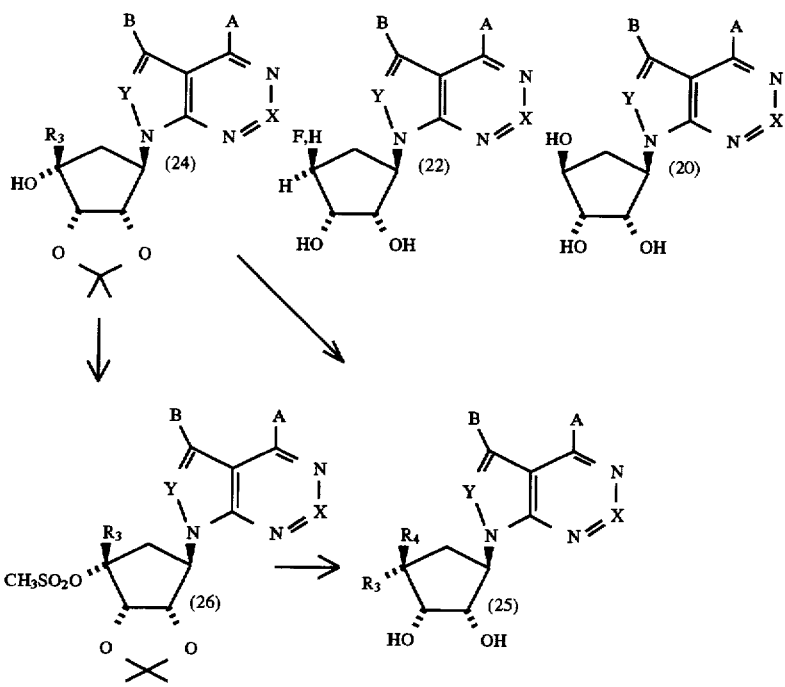

An alternative method for the synthesis of compound 25 involves condensation of ketone 23 (where A, B, X, and Y are defined in the claims) with substituted amines to give 27, as depicted in Scheme 8. This can be reduced with sodium borohydride to give 28 ($R_3$=H), or reacted with organometallic reagents to give 28 ($R_3$=loweralkyl). These compounds can be deprotected with aqueous acid to give compound 25 ($R_3$=H, loweralkyl; $R_4$=RNH).

Scheme 8.

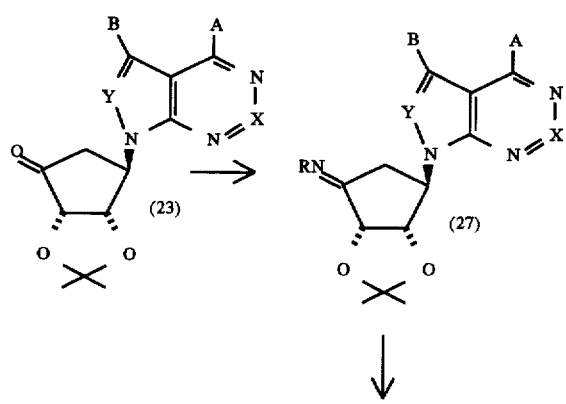

-continued
Scheme 8.

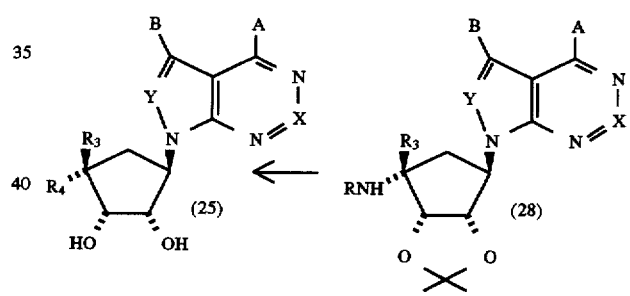

In cases where A is desired to be hydroxyl or substituted oxygen, compounds where A=Cl (prepared as described above) can be treated with a metal salt of an alcohol (for example sodium methoxide) at elevated temperature, as described by Townsend (J. Med. Chem. (1988), 31, 2086–2092). In cases where A is desired to be a thioether or substituted sulfur, compounds where A=Cl (prepared as described above) can be treated with a metal salt of a mercaptan (for example the sodium salt of ethanethiol) at elevated temperature, as described above. In cases where A is desired to be amine, or substituted amine, compounds where A=Cl (prepared as described above) can be treated with ammonia or the amino (for example methylamine or morpholine) at elevated temperature, as described above.

In cases where A is desired to be a urea, compounds where A=$NH_2$ (synthesized as described above) can be prepared by treatment with an sodium isocyanide in acid, or with an isocyanate (for example, methyl isocyate) in basic solution. In cases where A is desired to be a carbamate, compounds where A=NH₂ (synthesized as described above) can be prepared by treatment with a substituted chloroformate ester (for example, phenyl chloroformate) in basic solution. In cases where A is desired to be an amide, compounds where A=NH₂ (synthesized as described above) can be prepared by treatment with a substituted acyl chloride (for example benzoyl chloride) in pyridine. In cases where A is desired to be a halogen other than chlorine, compounds where A=Cl (synthesized as described above) can be prepared by treatment with the corresponding mineral acid (for example hydrobromic acid), or by treatment with the copper(I) salt of the halide, for example (copper(I)iodide) at elevated temperature.

In cases where B is desired to be an alkyl group, compounds 25 where B=I or Br, can be subjected to the Negishi modification of the Stille coupling. In this case, the halogenated compound is treated with an alkyl zinc reagent in the presence of a catalytic amount of a palladium complex, like Pd(PPh₃)₄ or PdCl2(PPh3)₂. In cases where B is desired to be aryl, heteroaryl, alkyl-substituted alkenyl, or aryl-substituted alkenyl, the compounds 25 where B=I or Br, can be subjected to the Stille reaction. In this case, the halogenated compound is treated with a appropriately substituted organostannane or sodium carbonate and an organoboronic acid reagent, in the presence of a catalytic amount of a palladium complex, like Pd(PPh₃)₄ or PdCl₂(PPh₃)₂.

The halogenated heterocycles 29 (where B=Br, I, and A, X, Y, R₃, R₄) can also be convened to compounds, where B=CO₂CH₃, by treatment of 29 with a Pd catalyst in methanol under an atmosphere of carbon monoxide (Bergstrom, J. Org. Chem. (1981) 46, 1423–1431). Sodium hydroxide induced hydrolysis gives the acid 30, which can be convened to the corresponding amides 31 by treatment with diphenylphoryl azide or carbonyl diimidazole, followed by treatment with an amine as shown in Scheme 9 (Ann. Reviews in Biochemistry, (1970) 39, 841). In cases where protection of the 2',3' hydroxyls (R₁=R₂=OH) is required, 29 can be protected as the acetonide as described for compound 21, and following synthetic transformation, deprotected to give 31, as described for the transformation of compound 24 into compound 25.

Scheme 9.

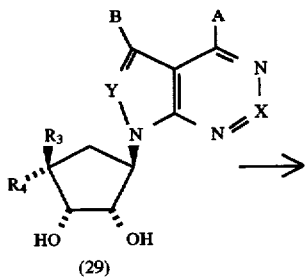

(29)

-continued
Scheme 9.

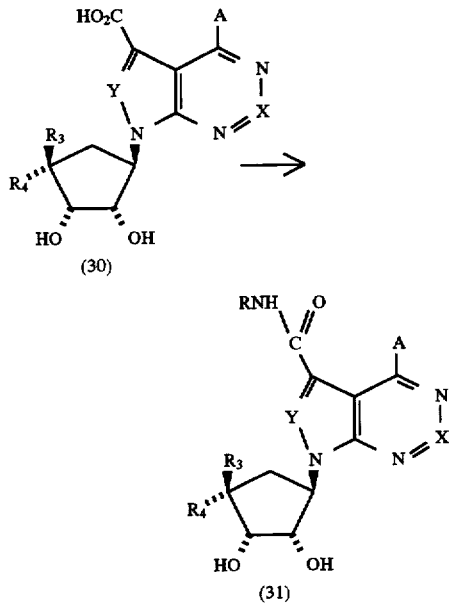

(30)

(31)

In cases where B is desired to be an alkoxy group, compounds 29 where B=I or Br, can be treated with an alkoxide salt and a catalytic amount of a copper salt like copper(I)iodide at elevated temperature. In cases where B is desired to be a cyano group, compounds 29 where B=I or Br, can be treated with copper(I)cyanide at elevated temperature.

Scheme 10.

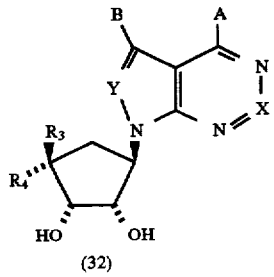

(32)

In cases where R₃ or R₄ are desired to be substituted nitrogen, the compounds 32, where R₃ or R₄ are NH₂ (prepared as described above), can reductively alkylated with aldehydes (for example, formaldehyde) in the presence of sodium cyanoborohydride (Borcht reduction), or in the presence of formic acid (Eschweiler-Clark reaction). In cases where R₃ or R₄ are desired to be substituted amino, compounds where R₃ or R₄ are NH₂ can be reacted with electrophilic halogenated heterocycles (like 3,6-dichloropyridazine), with electrophilic haloaromatics (like 2-fluoronitrobenzene), or with substituted alkyl halides (like benzyl chloride).

In cases where R₃ or R₄ is desired to be a urea, compounds where R₃ or R₄=NH₂ (synthesized as described above) can be treated with potassium cyanate in acid (L. P. Walls J. Chem. Soc. (1946), 1031), or with an isocyanate (for example, methyl isocyanate) in basic solution (T. L. Hough, et al. J. Heterocyclic Chem. (1986) 23, 1125). In cases where R₃ or R₄ is desired to be a carbamate, compounds where R₃ or R₄=NH₂ (synthesized as described above) can be prepared by treatment with a substituted chloroformate ester (for example, phenyl chloroformate) in basic solution. In cases where $R_3$ or $R_4$ is desired to be an amide, compounds where $R_3$ or $R_4$=$NH_2$ (synthesized as described above) can be prepared by treatment with a substituted acyl chloride (for example, propionyl chloride) in pyridine or basic solution. In cases where $R_3$ or $R_4$ is desired to be a sulfonamide, compounds where $R_3$ or $R_4$=$NH_2$ (synthesized as described above) can be prepared by treatment with a substituted sulfonyl chloride (for example methanesulfonyl chloride) in basic solution. In cases where $R_3$ or $R_4$ is desired to be a sulfamate, compounds where $R_3$ or $R_4$=OH (synthesized as described above) can be prepared by treatment with $H_2NSO_2Cl$ in the presence of a base (for example, sodium hydride) as described by Vince (J. Med. Chem. (1992) 35, 3991–4000).

In cases where $R_1$ and $R_2$ are desired to be for instance O-acyl or O(C=O)O, the compounds where $R_1$ and $R_2$ are OH can be treated with an acyl chloride in pyridine to provide $R_1$,$R_2$=Oacyl, or with carbonyl diimidazole in pyridine or DMF to provide the carbonate where $R_1$, $R_2$ is O(C=O)O.

Compounds where $R_1$=$R_2$=H can be prepared by hydrogenating the corresponding olefinic compounds with platinum oxide and hydrogen gas. The compounds where $R_1$=—H, $R_2$=OH and $R_1$=OH, $R_2$=H can be prepared from the corresponding olefinic compounds by hydroboration using borane followed by oxidation with N-methylmorpholine oxide.

One of ordinary skill in the art will readily appreciate that the generalized Schemes 1–10 set forth above are exemlary and that similar procedures can be used to prepare compounds having other substituents, stereochemistry and other like modifications.

A detailed description of the synthesis of numerous inhibitor compounds of the present invention is set forth hereinafter in the Examples.

The present invention also provides synthetic intermediates useful in making the inhibitor compound of the present invention. Certain intermediates in the production of compounds of the present invention likely have use as prodrugs.

The term "prodrug" refers to compounds that are rapidly transformed in vivo to yield the parent compounds of Formula (I), as for example, by hydrolysis in blood. T. Higuchi and V. Stella provide a thorough discussion of the prodrug concept in *Prodrugs as Novel Delivery Systems*, Vol. 14 of the A.C.S. Symposium Series, American Chemical Society (1975). Examples of esters useful as prodrugs for compounds containing carboxyl groups can be found on pages 14–21 of *Bioreversible Carriers in Drug Design: Theory and Application*, edited by E. B. Roche, Pergamon Press (1987).

The term "prodrug ester group" refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

Exemplary such compounds are:

N7-((1'R,2'S,3'S,4'S)-2',3'-dihydroxy-4'-(t-butyldimethylsilyloxy)-cyclopentyl)-4-chloro-pyrrolopyrimidine;

N7-((1'R,2'S,3'R,4'S)-2',3',4'-triacetoxycyclopentyl)-4-cholor-5-phenyl-pyrrolopyrimidine;

N7-((1'R,2'S,3'R,4'S)-2',3',4'-triacetoxyclopentyl)-4,5-bis-phenylacetylenyl-pyrrolopyrimidine and N7-((1'R, 2'S,3'R,4'S)-2',3',4'-triacetoxycyclopentyl)-4-chloro-5-phenylacetylenyl-pyrrolopyrimidine;

N7-((1'R,2'S,3'R,4'S)-2',3',4'-triacetoxycyclopentyl)-4,5-dichloro-pyrrolopyrimidine;

N7-((1'R,2'S,3'R, 4'S)-2',3'- dihydroxy-4'-(trifluoroacetyl) amino-cyclopentyl)-4-chloro-5-iodo-pyrrolopyrimidine and N7-((1'R,2'S,3'R,4'S)-2',3'-(trifluoroacetyl)amino-cyclopentyl)-4-hydroxy-5-iodo-pyrrolopyrimidine;

N7-((1'R,2'S,3'R,4'S)-2',3'—O-(2"-oxo-1",3"-dioxayl)-4'-amino-cyclopentyl)-4chloro-5-iodo-pyrrolopyrimidine;

N7-((1'R,2'S,3'R,4'S)-2',3'-diacetoxy-4'-(acetyl)amino-cyclopentyl)-4-chloro-5-iodo-pyrrolopyrimidine;

N7-((1'R,2'S,3'R,4'S)-2',3'—O-(2"-oxo-1",3"-dioxalyl)-4'-(acetyl)amino-cyclopentyl)-4-chloro-5-iodo-pyrrolopyrimidine and N7-((1'R,2'S,3'R,4'S)-2',3'—O-( 2"-oxo-1",3"-dioxalyl)-4'-(acetyl)amino-cyclopentyl)-4-hydroxy-5-iodo-pyrrolopyrimidine;

N7-((1'R,2'S,3'R,4'S)-2',3'-dihydroxy-4'-(acetyl)amino-cyclopentyl-4-chloro-5-iodo-pyrrolopyrimidine;

N7-((1'R,2'S,3'R,4'S)-2',3'-dihydroxy-4'-(acetyl)amino-cyclopentyl-4-amino-5-iodo-pyrrolopyrimidine;

N7-((1'R,2'S,3'R,4'S)-2',3'-dihydroxy-4'-(3"-nicotinoyl) amino-cyclopentyl)-4-chloro-5-iodo-pyrrolopyrimidine; and N7-((1'R,2'S,3'R,4'S)-2',3'-diacetoxy-4'-(acetyl)amino-cyclopentyl)-4-amino-5-iodo-pyrrolopyrimidine.

V. Process of Inhibiting Kinase

In yet another aspect of the present invention a process of inhibiting adenosine kinase is disclosed. In accordance with that process, an adenosine kinase enzyme is exposed to an effective inhibiting amount of an adenosine kinase inhibitor compound of the present invention. Preferred such compounds for use in the process are the same as set forth above. Means for determining an effective inhibiting amount are well known in the art.

The adenosine kinase to be inhibited can be located in vitro, in situ or in vivo. Where the adenosine kinase is located in vitro, adenosine kinase is contacted with the inhibitor compound, typically by adding the compound to an aqueous solution containing the enzyme, radiolabeled substrate adenosine, magnesium chloride and ATP. The enzyme can exist in intact cells or in isolated subcellular fractions containing the enzyme. The enzyme is then maintained in the presence of the inhibitor for a period of time and under suitable physiological conditions. Means for determining maintained times are well known in the art and depend inter alia on the concentrations of enzyme and the physiological conditions. Suitable physiological conditions are those necessary to maintain adenosine kinase viability and include temperature, acidity, tonicity and the like. Inhibition of adenosine kinase can be performed, by example, according to standard procedures well known in the art (Yamada et at., *Comp. Biochem. Physiol.* 1982, 71B: 367–372).

Where the adenosine kinase is located in situ or in vivo, is typically administered to a fluid perfusing the tissue containing the enzyme. That fluid can be a naturally occurring fluid such as blood or plasma or an artificial fluid such as saline, Ringer's solution and the like. A process of inhibiting adenosine kinase in vivo is particularly useful in mammals such as humans. Administering an inhibitor compound is typically accomplished by the parenteral (e.g., intravenous injection or oral) administration of the compound. The amount administered is an effective inhibiting or therapeutic amount.

Compounds of the present invention inhibit adenosine kinase activity in vitro and in vivo. In vitro adenosine kinase activity can be measured using any of the standard procedures well known in the art. By way of example, cells containing adenosine kinase, such as IMR-32 human neuroblastoma cells, are cultured in the presence and absence of an inhibitor. Inhibition is measured as the ability to inhibit phosphorylation of endogenous or externally applied $^{14}C$-adenosine by these cells. The cells can be intact or broken. The specificity of adenosine kinase inhibitory activity is determined by studying the effects of inhibitors on adenosine A1 and A2a receptor binding, adenosine deaminase activity and adenosine transport.

By a "therapeutically-effective amount" of the compound of the invention is meant a sufficient amount of the compound to treat disorders, at a reasonable benefit/risk ratio applicable to any medical treatment. It will be understood, however, that the total daily usage of the compounds and compositions of the present invention is to be decided by the attending physician within the scope of sound medical judgment. The specific therapeutically effective dose level for any particular patient will depend upon a variety of factors including the disorder being treated and the severity of the disorder, activity of the specific compound employed; the specific composition employed; the age, body weight, general health, gender and diet of the patient; the time of administration, route of administration, and rate of excretion of the specific compound employed; the duration of the treatment; drugs used in combination or coincidental with specific compound employed; and the like factors well known in the medical arts and well within the capabilities of attending physicians.

Compounds of the present invention are effective in inhibiting a adenosine kinase activity in vivo. Numerous animal models for studying adenosine kinase activity and the affects of inhibiting such activity are well known in the art. By way of example, adenosine kinase inhibitors have been reported to protect rodents (e.g., mice and rats) from seizures induced by the subcutaneous administration of pentylenetetrazol (PTZ). Typically the rodents are injected with various doses of a given inhibitor followed at various times by the subcutaneous administration of from about 10 to about 500 milligrams per kilogram of PTZ. The injected animals are then observed for the onset of seizures.

Numerous other animal models of adenosine kinase activity have been described [See, e.g., Davies, et al., *Biochem. Pharmacol.*, 33:347–355 (1984); Keil et al., *Eur. J. Pharmacol*, 271: 37–46 (1994); Murray et al., *Drug Development Res.*, 28: 410–415 (1993)].

Numerous inhibitor compounds of the present invention were tested in vitro and found to inhibit adenosine kinase activity. The results of some representative studies are shown below in Tables 1 and 2.

TABLE 1

| $R_5$ | $R_6$ | $IC_{50}(\mu M)$ |
|---|---|---|
| Cl | Cl | 0.090 |
| Cl | I | 0.010 |
| $NH_2$ | I | 0.013 |
| NHPh | I | 0.10 |
| Cl | Ph | 0.045 |
| $NH_2$ | Ph | 0.20 |
| NHPh | Ph | 0.003 |
| PhC≡C | PhC≡C | 0.015 |
| Cl | PhC≡C | 0.10 |
| $NH_2$ | PhC≡C | 0.23 |
| $NH_2$ | $PhCH_2CH_2$ | 0.30 |

TABLE 1-continued

| $R_4$ | $R_5$ | $R_6$ | $IC_{50}(\mu M)$ |
|---|---|---|---|
| $H_2N$ | Cl | I | 0.000035 |
| $H_2N$ | $NH_2$ | I | 0.000080 |
| $Boc_2N$ | Cl | I | >1 |
| NHBoc | $NH_2$ | I | 0.015 |
| $CH_3NH$ | Cl | $CH_3$ | 0.3 |
| $(CH_3)_2N$ | Cl | I | 0.02 |

$IC_{50} = 2.5$ nM

TABLE 2

| $R_5$ | $R_6$ | $IC_{50}$ ($\mu M$) |
|---|---|---|
| Cl | Cl | |
| Cl | I | >10 |
| Cl | Ph | >100 |
| PhC≡C | PhC≡C | >100 |
| | | >10 |

| $R_5$ | | $IC_{50}$ ($\mu M$) |
|---|---|---|
| Cl | | >10 |

| $R_5$ | R | $IC_{50}$ ($\mu M$) |
|---|---|---|
| Cl | $CF_3CO$ | |
| OH | $CF_3CO$ | 0.11 |
| Cl | $CH_3CO$ | 0.20 |
| $NH_2$ | $CH_3CO$ | 0.35 |
| $NH_2$ | NHBoc | 0.16 |
| | | 0.15 |

| R | $IC_{50}$ ($\mu M$) |
|---|---|
| $CH_3OCO$ | 0.30 |
| | 0.005 |

TABLE 2-continued

[Structure: pyrrolopyrimidine with I, R5, R substituents; RNH-cyclopentyl-diacetate]

| R | R5 | IC50 (µM) |
|---|----|-----|
| H | Cl | |
| CH3CO | Cl | 0.0025 |
| CH3CO | OH | 6.3 |
| | | 4.0 |

VI. Process of Treating Cerebral Ischemia, Epilepsy, Nociception, Inflammation or Sepsis In yet another aspect of the present invention a method of treating cerebral ischemia, epilepsy, nociception, inflammation and sepsis in a human or lower mammal is disclosed, comprising administering to the patient a therapeutically effective amount of a compound.

Alterations in cellular adenosine kinase activity have been observed in certain disorders. Adenosine kinase activity was found to be decreased, relative to normal liver, in a variety of rat hepatomas: activity of the enzyme giving a negative correlation with tumor growth rate (Jackson et at., Br. J. Cancer, 1978, 37: 701–713). Adenosine kinase activity was also diminished in regenerating liver after partial hepatectomy in experimental animals (Jackson et al., Br. J. Cancer, 1978, 37: 701–713). Erythrocyte Adenosine kinase activity was found to be diminished in patients with gout (Nishizawa et al., Clin. Chim. Acta 1976, 67: 15–20). Lymphocyte adenosine kinase activity was decreased in patients infected with the human immunodeficiency virus (HIV) exhibiting symptoms of AIDS, and increased in asymptomatic HIV-seropositive and HIV-seronegative high-risk subjects, compared to normal healthy controls (Renouf et at., Clin. Chem. 1989, 35: 1478–1481). It has been suggested that measurement of adenosine kinase activity may prove useful in monitoring the clinical progress of patients with HIV infection (Renouf et at., Clin. Chem. 1989, 35: 1478–1481).

The following Examples illustrate preferred embodiments of the present invention and are not limiting of the specification and claims in any way.

EXAMPLE 1

Synthesis of (1R,4S)-cis-4-(t-butyldimethylsilyloxy)-1-acetoxy-2-cyclopentene:

A mixture of 710 mg of (1R,4S)-cis-4-hydroxy-2-cyclopentenyl acetate, 1.21 g of t-butyldimethylsilylchloride, and 1.09 g of imidazole in 1.7 mL of dimethylformamide was stirred at 25° C. for six hours, then poured into a mixture of ethyl acetate/hexane and washed with sodium phosphate buffer (pH 7). The organic phase was dried (MgSO4), concentrated in vacuo, and purified by flash chromatography, eluting with ethyl acetate/hexane, to give 1.08 g of a thin clear oil. Mass spectrum: [M+H] m/z 257. Analysis: ($C_{13}H_{24}SiO_3$) found: C 60.90, H 9.43. $[\alpha]_D^{25}$=−0.80° (c=1.8, $CH_2Cl_2$).

EXAMPLE 2

Synthesis of N7-((1'R,4'S)-cis-4-(t-butyldimethylsilyloxy)-2'-cyclopentenyl)-4-chloro-pyrrolopyrimidine:

A mixture of 216 mg of 4-chloropyrrolopyrimdine (L. B. Townsend reference), 297 mg of (1R,4S)-cis-4-(t-butyldimethylsilyloxy)-1-acetoxy-2-cyclopentene, 11.3 mg of lithium hydride, 225 mg of triphenylphosphine, and 129 mg of tris(dibenzylidineacetone)dipalladium (0) (Aldrich) in 1.4 mL of dimethylsulfoxide was heated with stirring under nitrogen at 70° C. for 18 hours, then poured into ethyl acetate and washed with sodium phosphate buffer (pH 7). The organic phase was dried (MgSO4), and concentrated in vacuo. The resulting oil was dissolved in $CH_2Cl_2$/hexane and purified by flash chromatate/hexane, to give the title compound as a clear oil. Mass spectrum: [M+H] m/z 350. Analysis: ($C_{17}H_{24}SiClN_3O$·0.2 ethyl acetate) found: C 57.82, H 6.66, N 11.10. $[\alpha]_D^{25}$=+35.94° (c−1.1, $CH_2Cl_2$).

EXAMPLE 3

Synthesis of N7-((1R,2'S,3'R,4'S)-2',3',4'-trihydroxycyclopentyl)-4-chloro-5-iodo-pyrrolopyrimidine:

A mixture of 250 mg of N7-((1'R,2'S,3'R,4'S)-2',3',4'-triacetoxycyclopentyl)-4-chloro-5-pyrrolopyrimidine in methanol was saturated with ammonia and stirred under nitrogen at 25° C. for 60 hours. Concentration in vacuo gave a white solid which was recrystallized from ethanol/water to give 140 mg of clear plates, mp 206°–207° C. Mass spectrum: [M+H] m/z 396. Analysis: $C_{11}H_{11}N_3O_3ICl$ found: C 33.68, H2.61, N 10.55. $[\alpha]_D^{25}$=−40.12° (c=0.33, $CH_3OH$).

EXAMPLE 4

Synthesis of N7-((1'R,2'S,3'S,4'S)-2',3'-dihydroxy-4'-(t-butyldimethylsilyloxy)-cyclopentyl)-4-chloro-pyrrolopyrimidine:

A mixture of 312 mg of N7-((1'R,4'S)-cis-4'-(t-butyldimethylsilyloxy)-2-cyclopentenyl)-4-chloro-pyrrolopyrimidine, 1.1 g of N-methylmorpholine-N-oxide, and 2 mL of a 2.5% solution of osmium tetroxide solution in t-butanol, in 3 mL of t-butanol and 2 mL of tetrahydrofuran was stirred under nitrogen at 8° C. for 30 minutes, then poured into ethyl acetate and washed with sodium phosphate buffer (pH 7) and saturated NaCl solution. The organic phase was dried (Na2SO4), and concentrated in vacuo. The resulting oil was purified by flash chromatography, eluting with ethanol/$CH_2Cl_2$, to give the title compound as a white solid, mp 164°–165° C. Mass spectrum: [M+H] m/z 384. Analysis: ($C_{17}H_{26}N_3O_3SiCl$) found: C 53.23, H 6.91, N 10.93. $[\alpha]_D^{25}$=+9.58° (c=0.7, $CH_2Cl_2$).

EXAMPLE 5

Synthesis of N7-((1'R,2'S,3'R,4'S)-2',3',4'-triacetoxycyclopentyl)-4-chloro-pyrrolopyrimidine:

A mixture of 947 mg of N7-((1'R,2'S,3'S,4'S)-2',3'-dihydroxy-4'-(t-butyldimethylsilyloxy)-cyclopentyl)-4-chloro-pyrrolopyrimidine, 3 mL of a 1-M solution of tetra-(n-butyl)ammonium fluoride (TBAF) in THF, was stirred under nitrogen at 25° C. for 18 hours, then another 1 mL of 1-M TBAF solution was added. After six hours, the reaction was concentrated in vacuo, and 15 mL of pyridine, 63 mg of 4-dimethylaminopyridine (DMAP), and 1 mL of acetic anhydride were added. After stirring at 25° C. for 8 hours, the mixture was quenched with 0.5 mL of water and poured into ethyl acetate/hexane and washed with sodium phosphate buffer (pH 7), and water. The organic phase was dried (Na2SO4), and concentrated in vacuo. The resulting oil was purified by flash chromatography, eluting with ethyl acetate/hexane, followed by dissolving in chloroform and concentration to give 994 mg of a clear glass. Mass spectrum: [M+H] m/z 396. Analysis: ($C_{17}H_{18}N_3O_6Cl$ · 0.33 chloroform) found: C 47.88 H 4.17, N 9.55.

EXAMPLE 6

Synthesis of N7-((1'R,2'S,3'R,4'S)-2',3',4-triacetoxycyclopentyl)-4-chloro-5-iodo-pyrrolopyrimidine:

A mixture of 749 mg of N7-((1'R,2'S,3'R,4'S)-2+,3',4-triacetoxycyclopentyl)-4-chloro-pyrrolopyrimidine, 483 mg of sodium carbonate, 2.09 mL of a 1-M solution of ICl in $CH_2Cl_2$, and 4 mL $CH_2Cl_2$ was stirred under nitrogen at 25° C. for 18 hours. The mixture was poured into ethyl acetate and washed with a mixture of 10% sodium thiosulfate and saturated $NaHCO_3$. The organic phase was dried ($MgSO_4$), and concentrated in vacuo. The resulting oil was purified by flash chromatography, eluting with ethyl acetate/hexane, to give 729 mg of a white powder, mp 142°–143° C. Mass spectrum: [M+H]m/z 522. Analysis: found: $C_{17}H_{17}N_3)_6ICl$ found: C 39.35, H 3.21, N 7.97. $[\alpha]_D^{25}$=+0.55° (c=0.97, $CH_3OH$).

EXAMPLE 7

Synthesis of N7-((1'R,2'S,3'R,4'S)-2',3',4'-triacetoxycyclopentyl)-4-chloro-5-phenyl-pyrrolopyrimidine:

A mixture of 280 mg of N7-((1'R,2'S,3'R,4'S)-2',3',4'-triacetoxycyclopentyl)-4-chloro-5-iodo-pyrrolopyrimidine, 33 mg of triphenylarsine, 25 mg of tris(dibenzylidineacetone)dipalladium (0), and 154 mg of phenyltrimethylstannane in 3.5 mL of DMF was stirred under nitrogen at 65° C. for 19 hours. The mixture was poured into ethyl acetate and washed with water. The organic phase was dried ($MgSO_4$), and concentrated in vacuo. The resulting oil was purified by flash chromatography, eluting with ethyl acetate/hexane, to give 205 mg of a clear glass. Mass spectrum: [M+H] m/z 472.

EXAMPLE 8

Synthesis of N7-((1'R,2'S,3'R,4'S)-2',3',4'-trihydroxycyclopentyl)-4-amino-5-iodo-pyrrolopyrimidine:

A solution of 67 mg of N7-((1'R,2'S,3'R,4'S)-2',3',4'-trihydroxycyclopentyl)-4-chloro-5-iodo-pyrrolopyrimidine in methanol at 0° C. was saturated with ammonia, then heated in a sealed tube at 112° C. for 60 hours. Concentration in vacuo gave a black residue which was dissolved in DMF/methanol and purified by flash chromatography, eluting with methanol/ethyl acetate to give 46 mg of of a white powder, which was recrystallized from methanol/water to give long white needles, mp 233°–235° C. (dec.). Mass spectrum: [M+H] m/z 377. Analysis: $C_{11}H_{13}N_4O_3I.(0.1$ water) found: C 34.99, H 3.46, N 14.63. $[\alpha]_D^{25}$=−36.00° (c=0.20, $CH_3CH_2OH$).

EXAMPLE 9

Synthesis of N7-((1'R,2'S,3'R,4'S)-2',3',4'-trihydroxycyclopentyl)-4-chloro-5-phenyl-pyrrolopyrimidine:

A solution of 85 mg of N7-((1'R,2'S,3'R,4'S)-2',3',4'-triacetoxycyclopentyl)-4-chloro-5-phenyl-pyrrolopyrimidine in methanol at 0° C. was saturated with ammonia, then stirred at 25° C. for 24 hours in a sealed flask. Concentration in vacuo gave a semisolid mass which was purified by flash chromatography, eluting with ethanol/ethyl acetate to give 57 mg of of a white foam. Mass spectrum: [M+H] m/z 346. Analysis: $C_{17}H_{16}N_3O_3Cl.(0.5$ water)(0.25 ethyl acetate) found: C 57.41, H 5.00, N 11.03. $[\alpha]_D^{25}$=−44.19° (c=0.5, $CH_3OH$).

EXAMPLE 10

Synthesis of N7-((1'R,2'S,3'R,4'S)-2',3',4'-trihydroxycyclopetnyl)-4-(phenyl)amino-5-phenyl-pyrrolopyrimidine:

A solution of 102 mg of N7-((1'R,2'S,3'R,4'S)-2',3',4'-triacetoxycyclopentyl)-4-chloro-5-phenyl-pyrrolopyrimidine, 122 mg of triethylamine, and 179 mg of aniline in ethanol was stirred at 135° C. for 20 hours in a sealed robe. Concentration in vacuo gave a brown glass which was purified by flash chromatography, eluting with ethanol/ethyl acetate to give 29 mg of a white powder. This was recrystallized from methanol to give white needles, mp 193°–195° C. Mass spectrum: [M+H] m/z 403. Analysis: $C_{23}H_{22}N_4O_3.(1.0$ water) found: C 65.67, H 5.88, N 13.42. $[\alpha]_D^{25}$=−51.39° (c=0.25, 50% $CH_2Cl_2/CH_3OH$).

EXAMPLE 11

Synthesis of N7-((1R,2'S,3'R,4'S)-2',3',4'-triphydroxycyclopentyl)-4-amino-5-phenyl-pyrrolopyrimidine:

A solution of 102 mg of N7-((1'R,2'S,3'R,4'S)-2',3',4'-triacetoxycyclopentyl)-4-chloro-5-phenyl-pyrrolopyrimidine in methanol was saturated with ammonia at 0° C., then heated in a sealed vessel at 140° C. for 20 hours. Concentration in vacuo gave an orange syrup which was purified by flash chromatography, eluting with methanol/ethyl acetate to give 50 mg of a white powder, mp 90°–95° C. Mass spectrum: [M+H] m/z 327. Analysis: $C_{23}H_{22}N_4O_3.(1.0$ HCl)(0.5 acetamide) found: C 55.48, H 5.88, N 16.20. $[\alpha]_D^{25}$=−5.4° (c=1.0 $CH_3OH$).

EXAMPLE 12

Synthesis of N7-((1'R,2'S,3'R,4'S)-2',3'-dihydroxy-4'-amino-cyclopentyl)-4-chloro-5-iodo-pyrrolopyrimidine:

Dry hydrogen chloride gas was bubbled through a suspension of 108 mg of N7-((1'R,2'S,3'R,4'S)-2',3'-dihydroxy-4'-(bis-t-butoxycarbonylamino)-cyclopentyl)-4-chloro-5-iodo-pyrrolopyrimidine in diethyl ether at 25° C. until saturated. The mixture was stirred at 25° C. for 4 hours, then concentrated in vacuo. The residue was dissolved in methanol and concentrated in vacuo to a powder. Mass spectrum: [M+H] m/z 395. A portion of the sample was further purified by reversed phase (C18) high pressure liquid chromatography, eluting with methanol/50 mM ammonium acetate to give a white powder, mp>150° C. (decomp.). Analysis: $C_{11}H_{12}N_4O_2.ICl(0.4$ HCl)(1.1 acetic acid) found: C 33.32, H 3.88, N 11.57. IR (KBr) 2300–3600, 1580, 1410 $cm^{-1}$.

EXAMPLE 13

Synthesis of N7-((1'R,2'S,3'R,4'S)-2',3',4'-triacetoxycyclopentyl)-4,5-bis-phenylacetylenyl-pyrrolopyrimidine and $N_7$-((1'R,2'S,3'R,4'S)-2',3',4'-triacetoxycyclopentyl)-4-chloro-5-phenylacetylenyl-pyrrolopyrimidine:

A solution of 207 mg of N7-((1'R,2'S,3'R,4'S)-2',3',4'-triacetoxycyclopentyl)-4-chloro-5-iodo-pyrrolopyrimidine, 28 mg of bis(triphenylphosphine)palladium(II)dichloride, 7.6 mg of copper(I)iodide, 121 mg of phenylacetylene, and 4 mL of triethylamine in acetonitrile was heated at 60° C. for six hours. Concentration in vacuo gave a syrup which was purified by flash chromatography, eluting with $CH_2C_2$/ethyl acetate to give 144 mg of N7-((1'R,2'S,3'R,4'S)-2',3',4'-triacetoxycyclopentyl)-4,5-bis-phenylacetylenyl-pyrrolopyrimidine as a white glass. Mass spectrum: [M+H]

m/z 562. Analysis: $C_{33}H_{27}N_3O_6$.(0.4 ethyl acetate) found: C 69.50 H 4.93, N 7.08. $[\alpha]_D^{25}=-34.35°$ (c=1.0, ethylacetate).

Also obtained was 40 mg of N7-((1'R,2'S,3'R,4'S)-2',3',4'-triacetoxycyclopentyl)-4-chloro-5-phenylacetylenyl-pyrrolopyrimidine as a white glass: Mass spectrum: [M+H] m/z 496.

EXAMPLE 14

Synthesis of N7-((1R,2'S,3'R,4'S)-2',3',4-triacetodxycyclopentyl)-4,5-dichloro-pyrrolopyrimidine:

A mixture of 135 mg of N7-((1'R,2'S,3'R,4'S)-2',3',4-triacetoxycyclopentyl)-4-chloro-pyrrolopyrimidine and 46 mg of N-chlorosuccinimide in $CH_2Cl_2$ was stirred under nitrogen at 25° C. for 72 hours, then another 300 mg of N-chlorosuccinimide was added. After stirring for another 5 days, the mixture was quenched by adding 15% sodium thiosulfate/saturated sodium monohydrogen phosphate solution, then poured into ethyl acetate and washed with more 15% sodium thiosulfate/saturated sodium monohydrogen phosphate solution. The organic phase was dried ($MgSO_4$), and concentrated in vacuo. The resulting oil was purified by flash chromatography, eluting with ethyl acetate/dichloromethane, to give a white foam. Mass spectrum: [M+H] m/z 430. Analysis: $C_{17}H_{17}N_3O_6Cl_2$ found: C 47.58, H 4.08, N 9.50. $[\alpha]_D^{25}=+11.45°$ (c=1.05, ethyl acetate).

EXAMPLE 15

Synthesis of N7-((1'R,2'S,3'R,4'S)-2',3',4-trihydroxycyclopentyl)-4-chloro-5-phenylaceytylenyl-pyrrolopyrimidine:

A solution of 38 mg of N7-((1'R,2'S,3'R,4'S)-2',3',4'-triacetoxycyclopentyl)-4-chloro-5-phenylacetylenyl-pyrrolopyrimidine in methanol was cooled to 0° C. and saturated with ammonia. After stirring at 25° C. in a sealed flask for 24 hours, the solution was concentrated in vacuo to give a syrup which was purified by flash chromatography, eluting with methanol/ethyl acetate to give 32 mg of N7-((1'R,2'S,3'R,4'S)-2',3',4-trihydroxycyclopentyl)-4-chloro-5-phenylacetylenyl-pyrrolopyrimidine as a white glass. Mass spectrum: [M+H] m/z 370. Analysis: $C_{19}H_{16}N_3O_3Cl$.(0.5 methanol) found: C 60.61, H 4.48, N 10.90. $[\alpha]_D^{25}=-73.96°$ (c=0.34, methanol).

EXAMPLE 16

Synthesis of N7-((1'R,2'S,3'R,4'S)-2',3',4-trihydroxycyclopentyl)-4,5-dichloro-pyrrolopyrimidine:

A solution of 90 mg of N7-((1'R,2'S,3'R,4'S)-2',3',4-triacetoxycyclopentyl)-4,5-dichloro-pyrrolopyrimidine in methanol was saturated with ammonia. After stirring at 25° C. in a sealed flask for 16 hours, the solution was concentrated in vacuo to give a syrup which was purified by flash chromatography, eluting with methanol/ethyl acetate to give 75 mg of N7-((1'R,2'S,3'R,4S)-2',3',4'-trihydroxycyclopentyl)-4,5-dichloro-pyrrolopyrimidine as a white powder, mp 128–130° C. Mass spectrum: [M+H] m/z 304. Analysis: $C_{11}H_{11}N_3O_3Cl_2$.(0.5 water) found: C 42.26, H 4.04, N 13.26. $[\alpha]_D^{25}=-38.93°$ (c=0.45, methanol).

EXAMPLE 17

Synthesis of N7-((1'R,2'S,3'R,4'S)-2',3',4-trihydroxycyclopentyl)-4,5-bis-phenylacetylenyl-pyrrolopyrimidine:

A solution of 121 mg of N7-((1'R,2'S,3'R,4'S)-2',3',4-triacetoxycyclopentyl)-4,5-bis-phenylacetylenyl-pyrrolopyrimidine in methanol was saturated with ammonia. After stirring at 25° C. in a sealed flask for 16 hours, the solution was concentrated in vacuo to give a syrup which was purified by flash chromatography, eluting with methanol/ethyl acetate to give 75 mg of N7-((1'R,2'S,3'R,4'S)-2',3',4trihydroxycyclopentyl)-4,5-bis-phenylacetylenyl-pyrrolopyrimidine as a yellow powder. Mass spectrum: [M+H] m/z 436. Analysis: $C_{27}H_{21}N_3O_3$. (1.1 water) found: C 71.08, H 4.93, N 9.16. $[\alpha]_D^{25}=-81.73°$ (c=0.32, methanol).

EXAMPLE 18

Synthesis of N7-((1'R,2'S,3'R,4'S)-2',3',4-trihydroxycyclopentyl)-4-amino-5-phenylacetylenyl-pyrrolopyrimidine:

A solution of 169 mg of N7-((1'R,2'S,3'R,4'-trihydroxycyclopentyl)-4-chloro-5-iodo-pyrrolopyrimidine, 32 mg of bis(triphenylphosphine)palladium(II)dichloride, 8.7 mg of copper(I) iodide, 145 mg of phenylacetylene, and 4.5 mL of triethylamine in 5 mL of DMF was heated at 69° C. for six hours. Concentration in vacuo gave a syrup which was dissolved in water and lyophilized. The spongy foam was purified by flash chromatography, eluting with methanol/ethyl acetate to give N7-((1'R,2'S,3'R,4'S)-2',3',4-trihydroxycylopentyl)-4-amino-5-phenylacetylenyl-pyrrolopyrimidine as a yellow glass. Mass spectrum: [M+H] m/z 351. The glass was dissolved in aqueous HCl, then dried in vacuo to constant weight: Analysis: $C_{19}H_{18}N_4O_3$.(4.0 HCl) found: C 46.07, H 4.09, N 11.67. $[\alpha]_D^{25}=-45.57°$ (c=0.79, methanol).

EXAMPLE 19

Synthesis of N7-((1'R,4'R)-trans-4'-acetoxy-2'-cyclopentenyl)-4-chloro-5-iodo-pyrrolopyrimidine:

A mixture of 2.08 g of 4-chloro-5-iodopyrrolopyrimdine 882 mg of (1R,4S)-cis-4-(hydroxy)-1-acetoxy-2-cyclopentene, 1.95 g of triphenylphosphine, and 1.2 g of diethylazodicarboxylate in 20 mL of tetrahydrofuran was stirred under nitrogen at −25° C. for 22 hours, then concentrated in vacuo to a white paste. The paste was suspended in boiling ethyl acetate, and after cooling, filtered and washed with ethyl acetate then dried in vacuo to give 1.46 g of a fine white powder, mp 204° C. (decomp.). Mass spectrum: [M+H] m/z 404. Analysis: $(C_{13}H_{11}N_3O_2ICl)$ found: C 38.69, H 2.54, N 10.28. $[\alpha]_D^{25}=+183.65°$ (c=0.69, $CH_2Cl_2$). IR (KBr pellet) 1730 cm$^{-1}$.

EXAMPLE 20

Synthesis of N7-((1'R,4'R)-trans-4'-hydroxy-2'-cyclopentyl)-4-chloro-5-iodo-pyrrolopyrimidine:

A suspension of 4.68 g of N7-((1'R,4'R)-trans-4'-acetoxy-2'-cyclopentenyl)-4-chloro-pyrrolopyrimidine in methanol was cooled to 0° C. in an ice water bath and saturated with $NH_3$ and stirred under nitrogen at 25° C. for 40 hours, then concentrated in vacuo to a white solid The solid was suspended in boiling methanol, and after cooling, filtered and washed with methanol then dried in vacuo to give 3.58 g of a fine white powder. Mass spectrum: [M+H] m/z 362. Analysis: $(C_{11}H_9N_3OICl)$ found: C 36.60, H 2.50, N 11.82. IR (KBr pellet) 3100 cm$^{-1}$.

EXAMPLE 21

Synthesis of N7-((1'R,4'S)-cis-4'-(bis-t-butoxycarbonylamino)-2'-cyclopentenyl)-4-chloro-5-iodo-pyrrolopyrimidine:

To a mixture of 400 mg of N7-((1'R,4'R)-trans-4'-hydroxy-2'-cyclopentenyl)-4-chloro-5-iodo-pyrrolopyrimidine, 337 mg of di-t-butyl-imino dicarboxylate, 319 mg of di-t-butyl azodicarboxylate, and 363 mg of triphenylphosphine in a dry flask under nitrogen was added tetrahydrofuran. The reaction was stirred at 25° C. for 24 hours, then partitioned between ethyl acetate and water. The organic phase was dried (MgSO$_4$), concentrated in vacuo, and purified by flash chromatography, eluting with acetone/dichloromethane to give 464 mg of a white solid, mp 137°–142° C. Mass spectrum: [M+H] m/z 561. Analysis: (C$_{21}$H$_{26}$N$_4$O$_4$ICl. (0.21 di-t-butylamino dicarboxylate) found: C 45.09, H 4.90, N 10.97. IR (KBr pellet) 1740, 1705 cm$^{-1}$. [α]$_D^{25}$=+56.94° (c=0.71, dichloromethane).

EXAMPLE 22

Synthesis of N7-((1'R,2'S,3'R,4'S)-2',3'-dihydroxy-4'-(bis-t-butyoxycarbonylamino)-cyclopentyl)-4-chloro-5-iodo-pyrrolopyrimidine:

To a mixture of 400 mg of N7-((1'R,4'S)-cis-4'-(bis-t-butoxycarbonylamino)-2'-cyclopentenyl)-4-chloro-5-iodo-pyrrolopyrimidine, and 250 mg of N-morpholine-N-oxide in 1.5 mL of tetrahydrofuran at 0° C. was added 1.5 mL of a 2.5% solution of osmium tetroxide in t-butanol under nitrogen. The reaction was allowed to warm to 25° C. and stirred 2.5 hours, then poured into ethyl acetate and washed with a mixture of 10% sodium thiosulfate and sodium phosphate buffer (pH 7). The organic phase was dried (Na$_2$SO$_4$), concentrated in vacuo, and purified by flash chromatography, eluting with acetone/hexane to give 348 mg of a white solid. Mass spectrum: [M+H] m/z 595. Analysis: (C$_{21}$H$_{28}$N$_4$O$_6$ICl) found: C 42.57, H 4.74, N 9.24. [α]$_D^{25}$=−1.1° (c=0.46, ethyl acetate). IR (KBr) 3000–3650, 1740, 1700 cm$^{-1}$.

EXAMPLE 23

Synthesis of N7-((1'R,2'S,3'R,4'S)-2',3'-dihydroxy-4'-amino-cyclopentyl)-4-amino-5-iodo-pyrrolopyrimidine:

Dry hydrogen chloride gas was bubbled through a suspension of 108 mg of N7-((1'R,2'S,3'R,4'S)-2',3'-dihydroxy-4'-(t-butoxycarbonylamino)-cyclopentyl)-4-amino-5-iodo-pyrrolopyrimidine in diethyl ether at 25° C. until saturated. The mixture was stirred at 25° C. for 4 hours, then concentrated in vacuo. The residue was dissolved in methanol and concentrated in vacuo to a powder. Mass spectrum: [M+H] m/z 376. Analysis: (C$_{11}$H$_{14}$N$_5$O$_2$I) found: C 29.78, H 3.62, N 15.35. A portion of the sample was further purified by reversed phase (C18) high pressure liquid chromatography, eluting with methanol/50 mM ammonium acetate to give a white powder: IR (KBr) 2000–3600, 1630, 1405 cm$^{-1}$.

EXAMPLE 24

Synthesis of N7-((1'R,2'S,3'R,4'S)-2',3'-dihydroxy-4'-(trifluoroacetyl)amino-cyclopentyl)-4-chloro-5-iodo-pyrrolopyrimidine and N7-((1'R,2'S,3'R,4'S)-2',3'-dihydroxy-4'-(trifluoroacetyl)amino-cyclopentyl)-4-hydroxy-5-iodo-pyrrolopyrimidine:

To a solution of 136 mg of N7-((1'R,2'S,3'R,4'S)-2',3'-dihydroxy-4'-(bis-t-butoxycarbonylamino)-cyclopentyl)-4-chloro-5-iodo-pyrrolopyrimidine, in 5 mL of dioxane was added 5 mL of 4-M aqueous hydrochloric acid at 25° C. The reaction was stirred for 24 hours, after which 10 mL of water was added, and the mixture lyophilized. The resulting yellow powder was dissolved in methanol, and 0.28 mL of ethyl trifluoroacetate and 0.32 mL of triethylamine was added. After one hour, the reaction was poured into sodium phosphate buffer (pH 7) and extracted with ethyl acetate. The organic layer was washed with water, and saturated sodium chloride, dried over Na$_2$SO$_4$, and concentrated in vacuo. The residue was purified by flash chromatography, eluting with methanol/ethyl acetate/dichloromethane, to give N7-((1'R, 2'S,3'R,4'S)-2',3'dihydroxy-4'-(trifluoroacetyl)amino-cyclopentyl)-4-chloro-5-iodo-pyrrolopyrimidine as a clear oil: Mass spectrum: [M+H] m/z 491. $^1$H NMR (300 MHz, DMSO): δ1.91 (ddd, 1H), 2.63 (ddd, 1H), 3.93 (m, 1H), 4.12 (m, 1H), 4.30 (m, 1H), 5.07 (q, 1H), 5.15 (d, 1H), 5.24 (d, 1H), 8.13 (s, 1H), 8.63 (s, 1H), 9.54 (d, 1H).

Also isolated was N7-((1'R,2'S,3'R,4'S)-2',3'-dihydroxy-4'-(trifluoroacetyl)amino-cyclopentyl)-4-hydroxy-5-iodo-pyrrolopyrimidine as a clear glass: Mass spectrum: [M+H] m/z 473. $^1$H NMR (300 MHz, DMSO): 1.80 (ddd, 1H), 2.55 (ddd, 1H), 3.87 (m, 1H), 4.09 (m, 1H), 4.18 (m, 1H), 4.88 (q, 1H), 5.13 (d, 1H), 5.22 (d, 1H), 7.48 (s, 1H), 7.89 (d, 1H), 9.58 (d, 1H), 12.01 (d, 1H).

EXAMPLE 25

Synthesis of N7-((1'R,2'S,3'R,4'S)-2',3'-dihydroxy-4-(t-butoxycarbonylamino)-cyclopentyl)-4-amino-5-iodo-pyrrolopyrimidine:

A suspension of 1.2 g of N7-((1'R,2'S,3'R,4'S)-2',3'-dihydroxy-4'-(bis-t-butoxycarbonylamino)-cyclopentyl)-4-chloro-5-iodo-pyrrolopyrimidine in 20 mL of methanol was cooled to −50° C. and ammonia was bubbled through the solution until about 20 mL of ammonia had been condensed. The solution was heated at 129° C. in a sealed vessel for 14 hours, then cooled, and the ammonia allowed to evaporate. The methanol was removed by concentration in vacuo and the residue purified by flash chromatography, eluting with methanol/dichloromethane to give 777 mg of a white solid, mp 170°–171° C: Mass spectrum: [M+H] m/z 476. Analysis: (C$_{16}$H$_{22}$N$_5$O$_4$I) found: C 40.24, H 4.58, N 14.51. [α]$_D^{25}$= −28.51° (c=0.20, dichloromethane). IR (KBr) 3470, 3300, 3200, 1670, 1630 cm$^{-1}$.

EXAMPLE 26

Synthesis of N7-((1'R,2'S,3'R,4'S)-2',3'—O-(2"-oxo-1",3"-dioxalyl)-4'-amino-cyclopentyl)-4-chloro-5-iodo-pyrrolopyrimidine:

To a solution of 208 mg N7-((1'R,2'S,3'R,4'S)-2',3'-dihydroxy-4'-(bis-t-butoxycarbonylamino)-cyclopentyl)-4-chloro-5-iodo-pyrrolopyrimidine in 5 mL of DMF was added 57 mg of carbonyl diimidazole. After 5 hours at 25° C., an additional 57 mg of carbonyl diimidazole was added. After 24 hours, the reaction was poured into ethyl acetate/ hexane and washed with water, and saturated sodium chloride, dried over Na$_2$SO$_4$, and concentrated in vacuo, and passed over a short flash column, eluting with ethyl acetate/ dichloromethane. Concentration in vacuo of product-containing fractions gave N7-((1'R,2'S,3'R,4'S)-2',3'—O-(2"-oxo-1",3"-dioxalyl)-4'-(bis-t-butoxycarbonylamino)-cyclopentyl)-4-chloro-5-iodo-pyrrolopyrimidine. A solution of 217 mg of N7-((1'R,2'S,3'R,4'S)-2',3'—O-(2"-oxo-1",3"-dioxalyl)-4'-(bis-t-butoxycarbonylamino)-cyclopentyl)-4-chloro-5-iodo-pyrrolopyrimidine in ether was saturated with dry hydrogen chloride. After 2 hours, the reaction was concentrated in vacuo to a yellow paste of N7-((1'R,2'S,3'R, 4'S)-2',3'—O-(2"-oxo-1",3"-dioxalyl)-4'-amino-cyclopentyl)-4-chloro-5-iodo-pyrrolopyrimidine. Mass spectrum: [M+H] m/z 421. $^1$H NMR (300 MHz, CD$_3$OD): δ2.65–2.80 (m, 2H), 4.09 (ddd, 1H), 5.36 (dd, 1H), 5.44 (ddd, 1H), 5.68 (dd, 1H), 7.91 (s, 1H), 8.62 (s, 1H).

EXAMPLE 27

Synthesis of N7-((1'R,2'S,3'R,4'S)-2',3'-dihydroxy-4'-(acetyl)amino-cyclopentyl)-4-chloro-5-iodo-pyrrolopyrimidine:

To a solution of 154 mg of N7-((1'R,2'S,3'R,4'S)-2',3'-diacetoxy-4'-acetamido-2'-cyclopentyl)-4-chloro-5-iodo-pyrrolopyrimidine in methanol was saturated with ammonia. After stirring for 3.5 hours at 25° C., the reaction was concentrated in vacuo and the white powder recrystallized from ethanol/ethyl acetate to give a white powder, mp>245° C. (dec.) Mass spectrum: [M+H] m/z 437. Analysis: (C$_{13}$H$_{14}$N$_4$O$_3$ICl) found: C 35.79, H 3.32, N 12.60. IR (KBr) 2980–3620, 1645 cm$^{-1}$. $[\alpha]_D^{25}$=−17.42° (c=0.31, methanol).

EXAMPLE 28

Synthesis of N7-((1'R,2'S,3'R,4'S)-2',3'-diacetoxy-4'-(acetyl)amino-cyclopentyl)-4-chloro-5-iodo-pyrrolopyrimidine:

To a solution of 114 mg of N7-((1'R,2'S,3'R,4'S)-2',3'-dihydroxy-4'-amino-cyclopentyl)-4-chloro-5-iodo-pyrrolopyrimidine in pyridine at 25° C. was add&.d 147 mg of acetic anhydride. After stirring for three hours another 108 mg of acetic anhydride and 10 mg of DMAP (4-dimethylamino pyridine) was added. After a further 40 minutes, the reaction was quenched with 0.5 mL of water and poured into an ethyl acetate/dichloromethane mixture and washed with saturated sodium bicarbonate. The organic layer was dried over MgSO$_4$ and concentrated in vacuo to a syrup, which was purified by flash chromatography, eluting with methanol/dichloromethane, followed by another flash chromatography, eluting with acetonitrile/dichloromethane to give a clear glass. Mass spectrum: [M+H] m/z 521. Analysis: (C$_{17}$H$_{18}$N$_4$O$_5$ICl) found: C 39.46, H 3.59, N 10.48. IR (KBr) 3400, 3280, 1740, 1660 cm$^{-1}$. $[\alpha]_D^{25}$=−4.95° (c=0.93, methanol)

EXAMPLE 29

Synthesis of N7-((1'R,2'S,3'R,4'S)-2',3'-dihydroxy-4'-(acetyl)amino-cyclopentyl)-4-amino-5-iodo-pyrrolopyrimidine:

Ammonia was bubbled through a solution of 30 mg of N7-((1'R,2'S,3'R,4'S)-2',3'-diacetoxy-4'-(acetyl)amino-cyclopentyl)-4-amino-5-iodo-pyrrolopyrimidine in 4 mL of methanol for 20 seconds. After 12 hours, thin layer chromatography revealed that a single product was present, and the reaction was concentrated in vacuo, washed with water, and dried in vacuo. Mass spectrum: [M+H] m/z 418. $[\alpha]D^{25}$=−36.21° (c=1.0, 3:7 pyridine:methanol).

EXAMPLE 30

Synthesis of N7-((1'R,2'S,3'R,4'S)-2',3'—O-(2"-oxo-1",3"-dioxalyl)-4'-(acetyl)amino-cyclopentyl)-4-chloro-5-iodo-pyrrolopyrimidine and N7-((1'R,2'S,3'R,4'S)-2',3'—O-(2"-oxo-1",3"-dioxalyl)-4"-(acetyl)amino-cyclopentyl)-4-hydroxy-5-iodo-pyrrolopyrimidine:

To a solution of 72 mg of N7-((1'R,2'S,3'R,4'S)-2',3'—O-(2"-oxo-1",3"-dioxalyl)-4'-amino-cyclopentyl)-4-chloro-5-iodo-pyrrolopyrimidine in 2.5 mL of pyridine at 0° C. was added 17.5 μL of acetic anhydride. After 7 hours at 0° C., the reaction was allowed to warm to 25° C., and an additional 2.5 μL of acetic anhydride was added. After 24 hours, the reaction was concentrated in vacuo, and the residue purified by flash chromatography, eluting with methanol/dichloromethane. Concentration in vacuo of product-containing fractions gave N7-((1'R,2'S,3'R,4'S)-2',3'—O-(2"-oxo-1",3"-dioxalyl)-4'-(acetyl)amino-cyclopentyl)-4-chloro-5-iodo-pyrrolopyrimidine. Mass spectrum: [M+H] m/z 463. $[\alpha]_D^{25}$=−6.94° (c=1.0, 3:7 pyridine/methanol).

Also isolated was N7-((1'R,2'S,3'R,4'S)-2',3'—O-(2"-oxo-1",3"-dioxalyl)-4'-(acetyl)amino-cyclopentyl)-4-hydroxy-5-iodo-pyrrolopyrimidine. Mass spectrum: [M+H] =445. $^1$H NMR (300 MHz, CD$_3$SOCD$_3$): δ1.87 (s, 3H), 2.20 (m, 1H), 2.36 (m, 1H), 4.40 (m, 1H), 5.02 (dd, 1H), 5.29 (m, 1H), 5.38 (dd, 1H), 7.48 (s, 1H), 7.96 (s, 1H), 8.31 (d, 1H), 12.11 (s, 1H).

EXAMPLE 31

Synthesis of N7-((1'R,2'S,3'R,4'S)-2',3',4-trihydroxycyclopentyl)-4-amino-5-((2-phenyl)ethyl)pyrrolopyrimidine:

A solution of 22 mg of N7-((1'R,2'S,3'R,4'S),-2',3',4'-trihydroxycyclopentyl)-4-amino-5-phenylacetylenyl-pyrrolopyrimidine and 20 mg of 10% palladium on carbon in methanol was stirred under an atmosphere of hydrogen for two weeks. The mixture was filtered, concentrated in vacuo, and purified by flash chromatography, eluting with methanol/ethyl acetate to give 14 mg of N7-((1'R,2'S,3'R,4'S)-2',3',4'-trihydroxycyclopentyl)-4-amino-5-((2-phenyl)-pyrrolopyrimidine as a white microcrystalline powder. Mass spectrum: [M+H] m/z 355. $[\alpha]_D^{25}$=−25.97° (c=0.33, methanol).

EXAMPLE 32

Synthesis of N7-((1'R,2'S,3'R,4'S)-2',3'-dihydroxy-4'-(methyl)amino-cyclopentyl)-4-chloro-5-methyl-pyrrolopyrimidine:

A mixture of 320 mg of N7-((1'R,2'S,3'R,4'S)-2',3'-dihydroxy-4'-(bis-t-butoxycarbonylamino)-cyclopentyl)-4-chloro-5-iodo-pyrrolopyrimidine, 261 mg of imidazole, and 387 mg of t-butyldimethylsilyl chloride in dimethylformamide was stirred at 25° C. for 24 hours, then poured into 65 mL of ethyl acetate and washed with sodium phosphate buffer (pH 7), water, then dried (Na$_2$SO$_4$), and concentrated in vacuo to give a clear oil. This was purified by flash chromatography, eluting with acetone/hexane to give 464 mg of N7-((1'R,2'S,3'R,4'S)-2',3'-bis(t-butyldimethylsiloxy)-4'-(bis-t-butyoxycarbonylamino)-2'-cyclopentyl)-4-chloro-5-iodo-pyrrolopyrimidine.

A solution of 325 mg of N7-((1'R,2'S,3'R,4'S)-2',3'-bis(t-butyldimethylsilyloxy)-4'-(bis-t-butoxycarbonylamino)-cyclopentyl)-4-chloro-5-iodo-pyrrolopyrimidine in diethyl ether was cooled to −78° C. under nitrogen, and 0.49 mL of a 1.7M solution of t-butyl lithium in pentane was added. After stirring at −78° C. for 20 minutes, 1.5 mL of HMPA (hexamethylphosphoric triamide), and 281 mg of iodomethane was added. This was stirred at −78° C. for two hours, then allowed to warm to −25° C. over 2 hours. The reaction was poured into ethyl acetate and washed with water, and dried over MgSO$_4$. The organic phase was concentrated in vacuo to a syrup, which was purified by flash chromatography, eluting with ethyl acetate/dichloromethane to give 135 mg of an oil, which was further purified by flash chromatography, eluting with diethyl ether/dichloromethane to give 43 mg of N7-((1'R,2'S,3'R,4'S)-2',3'-bis(t-butyldimethylsilyloxy)-4-(((t-butoxycarbonyl)methyl)amino)-cyclopentyl)-4-chloro-5-methyl-pyrrolopyrimidine as a white oil. Mass spectrum, [M+H] m/z 625.

To a solution of 43 mg of N7-((1'R,2'S,3'R,4'S)-2',3'-bis (t-butyldimethylsilyloxy)-4'-(((t-butoxycarbonyl)methyl) amino)-cyclopentyl)-4-chloro-5-methyl-pyrrolopyrimidine in THF was added 0.6 mL of a 1M solution of TBAF (tetra-n-butylammonium fluoride) in THF. After 2 hours, the reaction was poured into a dichloromethane/ethyl acetate mixture, and washed with water, then dried ($Na_2SO_4$), and concentrated in vacuo to a clear glass. This was purified by flash chromatography, eluting with methanol/ethyl acetate to give 25 mg of N7-((1'R,2'S,3'R,4'S)-2',3'-dihydroxy-4'-((t-butoxycarbonyl)methylamino)-cyclopentyl)-4-chloro-5-methyl-pyrrolopyrimidine.

24 mg of N7-((1'R,2'S,3'R,4'S)-2',3'-dihydroxy-4'-(((t-butoxycarbonyl)methyl)amino)-cyclopentyl)-4-chloro-5-methyl-pyrrolopyrimidine was dissolved in 1.9 mL of TFA (trifluoroacetic acid) and stirred at 25° C. for 90 minutes, then concentrated in vacuo. A mixture of chloroform/methanol was added and then removed by evaporation several times to remove excess TFA (trifluoroacetic acid). The residue was purified by flash chromatography, eluting with methanol/acetic acid to give 31 mg of N7-((1'R,2'S,3'R,4'S)-2',3'-dihydroxy-4'-(methyl)amino-cyclopentyl)-4-chloro-5-methyl-pyrrolopyrimidine as a clear glass. Mass spectrum: [M+H] m/z 297. Analysis ($C_{13}H_{17}N_4O_2Cl$. (2.0 $CF_3CO_2H$).(0.1 ethyl acetate). (0.8 methanol)) found: C 39.09, H 4.15, N 10.02. $[\alpha]_D^{25}$=−11.24 (c=0.35, methanol), IR (neat) 2800–3450, 1670 $cm^{-1}$.

EXAMPLE 33

Synthesis of N7-((1'R,2'S,3'R,4'S)-2',3'-dihydroxy-4'-(methoxycarbonyl)amino-cyclopentyl)-4-chloro-5-iodo-pyrrolopyrimidine: To a solution of 78 mg of N7-((1'R,2'S, 3'R,4'S)-2',3'-dihydroxy-4'-amino-cyclopentyl)-4-chloro-5-iodo-pyrrolopyrimidine in pyridine was added 25 µL of triethylamine. The reaction was cooled to −30° C., and 20 µL of methyl chloroformate was added. A solid formed which dissolved on warming to −5° C. After 2 hours, the reaction was allowed to warm to 25° C., and after 3 days, concentrated in vacuo. The residue was dissolved in methanol and saturated with ammonia. After 24 hours, the reaction was concentrated in vacuo, and the residue purified by flash chromatography, eluting with methanol/ethyl acetate/ dichloromethane. Mass spectrum: [M+H] m/z 453. IR (neat) 3050–3550, 1710, 1580, 1450 $cm^{-1}$.

EXAMPLE 34

Synthesis of N7-((1'R,2'S,3'R,4'S)-2',3'-dihydroxy-4'-(3"-nicotinyl)amino-cyclopentyl)-4-chloro-5-iodo-pyrrolopyrimidine:

To a solution of 78 mg of N7-((1'R,2'S,3'R,4'S)-2',3'-dihydroxy-4'-amino-cyclopentyl)-4-chloro-5-iodo-pyrrolopyrimidine and 50 µL of triethylamine in 2 mL of pyridine at 0° C. was added 32 mg of nicotinyl chloride hydrochloride. After 10 minutes the reaction was allowed to warm to 25° C. and stirred for 7 days. After concentration in vacuo, the residue was taken up in toluene, whereupon a precipitate was produced. This was collected and triturated successively from water, methanol, and ethyl acetate, and dried in vacuo to give the title product. Mass spectrum: [M+H] m/z 500. IR (neat) 3050–3550, 1660, 1565, 1170 $cm^{-1}$.

EXAMPLE 35

Synthesis of N7-((1'R,2'S,3'R,4'S)-2',3'-diacetoxy-4'-(acetyl)amino-cyclopentyl)-4-amino-5-iodo-pyrrolopyrimidine:

To a solution of 75 mg of N7-((1'R,2'S,3'R,4'S)-2',3'-dihydroxy-4'-amino-cyclopentyl)-4-amino-5-iodo-pyrrolopyrimidine in 4 mL of pyridine was added 28 µL of triethylamine at 0° C. Acetic anhydride (75 µL) was added dropwise, and after one hour, the reaction was concentrated in vacuo and redissolved in 4 mL of pyridine, and 21 µL of acetic anhydride was added. After 24 hours, 28 µL of triethylamine was added, and after 24 hours, another 21 µL of acetic anhydride was added. The solution was concentrated in vacuo and residual solvent removed by azeotropic evaporation with toluene. Recrystallization from ethanol/ ethyl acetate gave a white solid. Mass spectrum: [M+H] m/z 502. $^1$H NMR (300 MHz, $CD_3SOCD_3$) δ1.87 (s, 3H), 1.90 (s, 3H), 1.98 (ddd, 1H), 2.07 (s, 3H), 2.57 (ddd, 1H), 4.22 (ddd, 1H), 5.09 (q, 1H), 5.20 (dd, 1H), 5.60 (dd, 1H), 6.65 (bs, 1H), 7.60 (s, 1H), 8.12 (s, 1H), 8.35 (d, 1H).

EXAMPLE 36

Synthesis of N7-((1'R,2'S,3'R,4'S)-2',3'-dihydroxy-4'-(dimethyl)amino-cyclopentyl)-4-chloro-5-iodo-pyrrolopyrimidine:

To a solution of 72 mg of N7-((1'R,2'S,3'R,4'S)-2',3'-dihydroxy-4'-amino-cyclopentyl)-4-chloro-5-iodo-pyrrolopyrimidine in 0.9 mL of 50 mM sodium phosphate buffer at pH 4.6 was added 0.12 mL of 37% formaldehyde and 30 mg of sodium cyanoborohydride. Acetic acid was added to adjust the pH to 4.5, and after stirring for 90 minutes at 25° C., the reaction was made basic with KOH and extracted with ethyl acetate. The organic phase was washed with saturated sodium chloride, dried, and concentrated in vacuo. The residue was dissolved in 1M HCl and lyophilized to a glass, which was purified by flash chromatography, eluting with methanol/ethyl acetate, to give a tan solid. The residue was further purified by high pressure liquid C18 reversed phase chromatography, eluting with methanol/50 mM ammonium acetate. Concentration gave a hygroscopic white glass. Mass spectrum: [M+H] m/z 423. Analysis: ($C_{13}H_{16}N_4O_2ICl$(1.2 acetic acid)(0.1 hydrochloric acid)(1.0 water) found: C 35.83, H 4.47, N 10.82. IR (KBr) 2800–3650 cm−1, 1575, 1530, 1500.

EXAMPLE 37

Synthesis of N1-((1'R,4'R)-trans-4'-acetoxy-2'-cyclopentenyl)-4-amino-3-bromo-pyrazolopyrimidine:

To a suspension of 3 mMoles of 4-amino-3-bromopyrazolopyrimidine, 3 mMole of (1R,4S)-cis-4-(hydroxy)-1-acetoxy-2-cyclopentene, and 3 mMole of triphenylphosphine in tetrahydrofuran is added 3 mMole of diethylazodicarboxylate. The reaction is stirred under nitrogen at 25° C. for 48 hours, then poured into ethyl acetate and washed successively with saturated sodium bicarbonate, saturated potassium bisulfate, and saturated sodium chloride solution. The organic layer is dried over $MgSO_4$, and concentrated in vacuo to afford the title compound.

EXAMPLE 38

Synthesis of N1-((1'R,4'R)-trans-4'-hydroxy-2'-cyclopentenyl)-4-amino-3-bromopyrazolopyrimdine:

A suspension of 1 mMole of N1-((1'R,4'R)-trans-4'-acetoxy-2'-cyclopentenyl)-4-amino-3-bromo-pyrazolopyrimdine in methanol is saturated with ammonia and stirred in a sealed vessel for 48 hours. Concentration in vacuo affords the title product.

EXAMPLE 39

Synthesis of N1-((1'R,4'S)-cis-4'-phthalimido-2'-cyclopentenyl)-4-amino-3-bromo-pyrazolopyrimdine:

To a mixture of 1 mMole of N7-((1'R,4'R)-trans-4'-hydroxy-2'-cyclopentenyl)-4-amino-3- bromopyrazolopyrimdine, 1 mMole of phthalimide, 1 mMole of diethylazodicarboxylate, and 1 mMole of triphenylphosphine in a dry flask under nitrogen is added tetrahydrofuran. The reaction is stirred at 25° C. for 24 hours, then concentrated in vacuo, and purified by flash chromatography.

EXAMPLE 40

Synthesis of N1-((1'R,2'S,3'R,4'S)-2',3'-dihydroxy-4'-phthalimido-cyclopentyl)-4-amino-3-bromo-pyrazolopyrimdine:

To a solution of 1 mMole of N1-((1'R,4'S)-cis-4'-phthalimido-2'-cyclopentenyl)-4-amino-3-bromo-pyrazolopyrimdine in t-butanol/tetrahydrofuran at 10° C is added 3 mMole of N-methylmorpholine-N-oxide and 0.2 mMole of solid osmium tetroxide. The mixture is allowed to warm to 25° C., stirred for 12 hours, then poured into dichloromethane and washed with a mixture of 10% sodium thiosulfate and sodium phosphate buffer (pH 7). The organic phase is dried ($Na_2SO_4$), concentrated in vacuo, and purified by flash chromatography to give the title compound.

EXAMPLE 41

Synthesis of N1-((1'R,2'S,3'R,4'S)-2',3'-dihydroxy-4'-amino-cyclopentyl)-4-amino-3-bromo-pyrazolopyrimdine:

To a suspension of 1 mMole of N1-((1'R,2'S,3'R,4'S)-2',3'-dihydroxy-4'-phthalimido-cyclopentyl)-4-amino-3-bromo-pyrazolopyrimdine in ethanol is added 5 mMole of hydrazine hydrate. The reaction is heated at reflux for 12 hours, cooled, and concentrated in vacuo. The residue is purified by flash chromatography to give the title compound.

EXAMPLE 42

Synthesis of N7-((1'R,2'S,3'R,4'S)-2',3'-dihydroxy-4'-(3"-chloro-pyridazin-6"-yl)amino-cyclopentyl)-4-amino-5-iodo-pyrrolopyrimidine:

A suspension of 1 mMole of N7-((1'R,2'S,3'R,4'S)-2',3'-dihydroxy-4'-amino-cyclopentyl)-4-amino-5-iodo-pyrrolopyrimidine and 3,6-dichloropyridazine in triethylamine/ethanol is heated in a sealed robe at 130° C. for six hours, then cooled, and the reaction concentrated in vacuo. The residue is purified by flash chromatography to give the product.

EXAMPLE 43

Synthesis of N7-((1'R,2'S,3'R,4'S)-2',3'-dihydroxy-4'-(3"-dimethylamino-pyridazin-6"-yl)amino-cyclopentyl)-4-amino-5-iodo-pyrrolopyrimidine:

A suspension of 1 mMole of N7-((1'R,2'S,3'R,4'S)-2',3'-dihydroxy-4'-(3"-chloro-pyridazinyl-6"-yl))amino-cyclopentyl)-4-amino-5-iodo-pyrrolopyrimidine in dimethylamine/ethanol is heated in a sealed tube at 130° C. for six hours, then cooled, and the reaction concentrated in vacuo. The residue is purified by flash chromatography to give the product.

EXAMPLE 44

Synthesis of N7-((1'R,2'S,3'R,4'S)-2',3'-dihydroxy-4'-(pyridin-2"-yl)amino-cyclopentyl)-4-amino-5-iodo-pyrrolopyrimidine:

A suspension of 1 mMole of N7-((1'R,2'S,3'R,4'S)-2',3'-dihydroxy-4'-amino-cyclopentyl)-4-amino-5-iodo-pyrrolopyrimidine and 20 mMole of 2-fluoropyridine in triethylamine/ethanol is heated in a sealed tube at 130° C. for six hours, then cooled, and the reaction concentrated in vacuo. The residue is purified by flash chromatography to give the product.

EXAMPLE 45

Synthesis of N7-((1'R,2'S,3'R,4'S)-2',3'-dihydroxy-4'-amino-cyclopentyl)-4-amino-5-phenyl-pyrrolopyrimidine:

A mixture of 1 mMole of N7-((1'R,2'S,3'R,4'S)-2',3'-dihydroxy-4'-(t-butoxycarbonyl)amino-cyclopentyl)-4-amino-5-iodo-pyrrolopyrimidine, 1.2 mMole of phenyltrimethylstannane, and 0.05 mMole of tetrakis-triphenylphosphine palladium (0) in DMF is heated at 70° C. for 12 hours, then cooled, and concentrated in vacuo to a syrup. The residue is purified by flash chromatography to give N7-((1'R,2'S,3'R,4'S)-2',3'-dihydroxy-4'-(t-butoxycarbonyl)amino-cyclopentyl)-4-amino-5-phenyl-pyrrolopyrimidine. This is dissolved in trifluoroacetic acid and after stirring at 25° C. for one hour, concentrated in vacuo to yield the title compound, N7-((1'R,2'S,3'R,4'S)-2',3'-dihydroxy-4'-amino-cyclopentyl)-4-amino-5-phenyl-pyrrolopyrimidine.

EXAMPLE 46

Synthesis of N7-((1'R,2'S,3'R,4'S)-2',3'-dihydroxy-4'-amino-cyclopentyl)-4-amino-5-methyl-pyrrolopyrimidine:

A mixture of 1 mMole of N7-((1'R,2'S,3'R,4'S)-2',3'-dihydroxy-4'-(t-butoxycarbonyl)amino-cyclopentyl)-4-amino-5-iodo-pyrrolopyrimidine, 1.2 mMole of tetramethylstannane ($Sn(CH_3)_4$), and 0.05 mMole of tetrakis-triphenylphosphine palladium (0) in DMF is heated at 70° C. for 12 hours, then cooled, and concentrated in vacuo to a dark syrup. The residue is purified by flash chromatography to give N7-((1'R,2'S,3'R,4'S)-2',3'-dihydroxy-4'-(t-butoxycarbonyl)amino-cyclopentyl)-4-amino-5-methyl-pyrrolopyrimidine. This is dissolved in trifluoroacetic acid and after stirring at 25° C. for one hour, concentrated in vacuo to yield the tide compound, N7-((1'R,2'S,3'R,4'S)-2',3'-dihydroxy-4'-amino-cyclopentyl)-4-amino-5-methyl-pyrrolopyrimidine.

EXAMPLE 47

Synthesis of N7-((1'R,2'S,3'R,4'S)-2',3'-dihydroxy-4'-amino-cyclopentyl)-4-amino-5-(pyridin-3-yl)pyrrolopyrimidine:

A mixture of 1 mMole of N7-((1'R,2'S,3'R,4'S)-2',3'-dihydroxy-4'-(t-butoxycarbonyl)amino-cyclopentyl)-4-amino-5-iodo-pyrrolopyrimidine, 1.2 mMole of 3-(tributylstannyl)-pyridine, and 0.05 mMole of tetrakis-triphenylphosphine palladium (0) in DMF is heated at 70° C. for 12 hours, then cooled, and concentrated in vacuo to a dark syrup. The residue is purified by flash chromatography to give $N_7$-((1'R,2'S,3'R,4'S)-2',3'-dihydroxy-4'-(t-butoxycarbonyl)amino-cyclopentyl)-4-amino-5-(pyridin-3-yl)-pyrrolopyrimidine. This is dissolved in trifluoroacetic acid and after stirring at 25° C. for one hour, concentrated in vacuo to yield the title compound, N7-((1'R,2'S,3'R,4'S)-2',3'-dihydroxy-4'-amino-cyclopentyl)-4-amino-5-(pyridin-3-yl)-pyrrolopyrimidine.

EXAMPLE 48

Synthesis of N7-((1'R,2'S,3'R,4'S)-2',3'-dihydroxy-4'-(1"-methylimidazole-4"-sulfonyl)amino-cyclopentyl)-4-amino-5-iodo-pyrrolopyrimidine:

To a suspension of 1 mMole of N7-((1'R,2'S,3'R,4'S)-2',3'-dihydroxy-4'-amino-cyclopentyl)-4-amino-5-iodopyrrolopyrimidine in triethylamine/pyridine at 0° C. is added 1 mMole of 1-methylimidazole-4-sulphonyl chloride (Maybridge Chemical Co.). The reaction is allowed to warm to 25° C., and stirred for 2 hours, concentrated in vacuo. The residue is purified by flash chromatography to give the product.

EXAMPLE 49

Synthesis of N7-((1R,4'S)-cis-4'-(pyridin-3'-yl)oxy-2'-cyclopentenyl)-4-chloro-5-iodo-pyrrolopyrimidine:

To a mixture of 1 mMole of N7-((1'R,4'R)-trans-4'hydroxy-2'-cyclopentyl)-4-chloro-pyrrolopyrimidine, 1 mMole of 3-hydroxypyridine, 1 mMole of di-t-butyl azodicarboxylate, and 1 mMole of triphenylphosphine is added dichloromethane in a dry flask under nitrogen. The reaction was stirred at 25° C. for 48 hours, then poured into ethyl acetate and extracted with aqueous hydrochloric acid (pH<1). The aqueous extract is made basic (pH>10) with ammonium hydroxide, and extracted with dichloromethane. The organic phase is dried ($Na_2SO_4$), concentrated in vacuo, and purified by flash chromatography to give the title compound.

EXAMPLE 50

Synthesis of N7-((1'R,4'S)-cis-4'-(acetylmercapto)-2'-cyclopentenyl-4-chloro-5-iodo-pyrrolopyrimidine:

To a mixture of 1 mMole of N7-((1'R,4'R)-trans-4'-hydroxy-2'-cyclopentyl)-4-chloro-pyrrolopyrimidine, 1 mMole of thiolacetic acid, 1 mMole of di-t-butyl azodicarboxylate, and 1 mMole of triphenylphosphine is added dichloromethane in dry flask under nitrogen. The reaction is stirred at 25° C. for 48 hours, then concentrated in vacuo, and purified by flash chromatography to give the title compound.

EXAMPLE 51

Synthesis of N7-((1'R,2'S,3'S,4'S)-2',3'-dihydroxy-4'-mercapto-cyclopentyl)-4-chloro-5-iodo-pyrrolopyrimidine:

To a solution of 1 mMole of N7-((1'R,4'S)-cis-4'-(acetylmercapto)-2'-cyclopentenyl)-4-chloro-5-iodo-pyrrolopyrimidine in t-butanol is added 1 mMole of solid osmium tetroxide. After stirring at 25° C. for 12 hours, hydrogen sulfide gas is bubbled through the reaction, followed by addition of 2M ammonia in methanol. After one hour, the reaction is concentrated in vacuo and the residue purified by flash chromatography to give the title compound.

EXAMPLE 52

Synthesis of N7-((1'R,4')-2',3'-dihydroxy-4'-(3"-picolylmercapto)-cyclopentyl)-4-chloro-5-iodo-pyrrolopyrimidine:

To a solution of 1 mMole of N7-((1'R,2'S,3'S,4'S)-2',3'-dihydroxy-4'-mercapto-cyclopentyl)-4-chloro-5-iodo-pyrrolopyrimidine in methanol is added 2 mMole of triethylamine and 1 mMole of 3-picolyl chloride hydrochloride. The mixture is slowly heated to reflux under nitrogen with stirring for one hour, then cooled and concentrated in vacuo. The residue is purified by flash chromatography to yield the title product.

EXAMPLE 53

Synthesis of N7-((1'R,2'S,3'S,4'S)-2',3'-dihydroxy-4'-(pyridin-2"-yl)mercapto-cyclopentyl)-4-chloro-5-iodo-pyrrolopyrimidine:

To a solution of 1 mMole of N7-((1'R,2'S,3'S,4'S)-2',3'-dihydroxy-4'-mercapto-cyclopentyl)-4-chloro-5-iodo-pyrrolopyrimidine in ethanol is added 2 mMole of triethylamine and 1 mMole of 2-fluoropyridine. The mixture is slowly heated to reflux under nitrogen with stirring for 24 hours, then cooled and concentrated in vacuo. The residue is purified by flash chromatography to yield the title product.

EXAMPLE 54

Synthesis of N7-((1'R,2'S,3'S,4'S)-2',3'-dihydroxy-4'-(methylmercapto)-cyclopentyl)-4-chloro-5-iodo-pyrrolopyrimidine:

To a solution of 1 mMole of N7-((1'R,2'S,3'S,4'S)-2',3'-dihydroxy-4'-mercapto-cyclopentyl)-4-chloro-5-iodo-pyrrolopyrimidine in methanol is added 2 mMole of triethylamine and 1 mMole of iodomethane. The mixture is slowly heated to reflux under nitrogen with stirring for 24 hours, then cooled and concentrated in vacuo. The residue is purified by flash chromatography to yield the title product.

EXAMPLE 55

Synthesis of N7-((1'R,2'S,3'S,4'S)-2',3'-dihydroxy,4'-((2"-amino)ethylmercapto)-cyclopentyl)-4-chloro-5-iodo-pyrrolopyrimidine:

To a solution of 1 mMole of N7-((1'R,2'S,3'S,4'S)-2',3'-dihydroxy-4'-mercapto-cyclopentyl)-4-chloro-5-iodo-pyrrolopyrimidine in methanol is added 2 mMole of triethylamine and 1 mMole of aziridine. The mixture is slowly heated to reflux under nitrogen with stirring for 2 hours, then cooled and concentrated in vacuo. The residue is purified by flash chromatography to yield the title product.

EXAMPLE 56

Synthesis of N7-((1'R,2'S,3'S,4'S)-2',3'-dihydroxy-4'-(pyridin-3'-yl)oxy-cyclopentyl)-4-chloro-5-iodo-pyrrolopyrimidine:

To a mixture of 0.1 mMole of N7-((1'R,4'S)-cis-4'-(3'-pyridyl)oxy-2'-cyclopentenyl)-4-chloro-5-iodo-pyrrolopyrimidine, 0.12 mMole of N-morpholine-N-oxide, and 0.3 mL of a 2.5% solution of osmium tetroxide in t-butanol at 0° C. is added tetrahydrofuran under nitrogen. The reaction is allowed to warm to 25° C. and stirred for 16 hours, then poured into ethyl acetate and washed with a mixture of 10% sodium thiosulfate and sodium phosphate buffer (pH 7). The organic phase is dried ($Na_2SO_4$), concentrated in vacuo, and purified by flash chromatography to give the title compound.

EXAMPLE 57

Synthesis of N7-((1'R,2'S,3'R,4'S)-2',3'-dihydroxy-4'-(t-butoxycarbonylamino)-cyclopentyl)-4-methoxy-5-iodo-pyrrolopyrimidine:

To a solution 1 mMole of N7-((1'R,2'S,3'R,4'S)-2',3'-dihydroxy-4'-(bis-t-butoxycarbonylamino)-cyclopentyl)-4-chloro-5-iodo-pyrrolopyrimidine in methanol is added 10 mMole of potassium methoxide. The solution is heated at 129° C. in a sealed vessel for 14 hours, then cooled. The methanol is removed by concentration in vacuo and the residue purified by flash chromatography to give the title product.

EXAMPLE 58

Synthesis of N7-((1'R,2'S,3'R,4'S)-2',3'-dihydroxy-4'-(t-butoxycarbonylamino)-cyclopentyl)-4-methoxy-5-carbomethoxy-pyrrolopyrimidine:

A solution 1 mMole of N7-((1'R,2'S,3'R,4'S)-2',3'-dihydroxy-4'-(t-butoxycarbonylamino)-cyclopentyl)-4-methoxy-5-iodo-pyrrolopyrimidine, 0.05 mMole of palladium diacetate, and 0.2 mMole of tri-ortho-toluylphosphine in methanol is placed under 5 atmospheres of carbon monoxide. The solution is heated at 100° C. in a sealed vessel for 48 hours, then cooled. The methanol is removed by concentration in vacuo and the residue purified by flash chromatography to give the title compound

EXAMPLE 59

Synthesis of N7-((1'R,2'S,3'R,4'S) 2',3'-dihydroxy 4'-(t-butoxycarbonylamino)-cyclopentyl)-4-methoxy-5-carboxy-pyrrolopyrimidine:

A solution 1 mMole of N7-((1'R,2'S,3'R,4'S)-2',3'-dihydroxy-4'-(t-butoxycarbonylamino)-cyclopentyl)-4-methoxy-5-carbomethoxy-pyrrolopyrimidine and 5 mMole of potassium hydroxide in aqueous tetrahydrofuran is heated at reflux until thin layer chromatography indicates complete ester hydrolysis, cooled, and the solvent removed in vacuo. The residue is suspended in aqueous methanol and carefully adjusted to pH 5 with aqueous hydrochloric acid. The mixture is diluted with saturated aqueous sodium chloride and extracted with dichloromethane. The organic phase is dried over $Na_2SO_4$, concentrated in vacuo, and the residue purified by flash chromatography to give the title compound.

EXAMPLE 61

Synthesis of N7-((1'R,2'S,3'R,4'S)-2',3'-dihydroxy-4'-amino-cyclopentyl)-4-methoxy-5-(N-cyclobutyl-carboxamido)pyrrolopyrimidine:

1 mMole of N7-((1'R,2'S,3'R,4'S)-2',3'-dihydroxy-4'-(t-butoxycarbonylamino)-cyclopentyl)-4-methoxy-5-(N-cyclobutyl-carboxamido)pyrrolopyrimidine was dissolved in trifluoroacetic acid at 10° C. and stirred for 10 minutes. The reaction was concentrated in vacuo, and purified by flash chromatography.

EXAMPLE 62

Synthesis of N7-((1'R,2'S,3'R,4'S)-2',3'-dihydroxy-4'-amino-cyclopentyl)-4-amino-5-cyano-pyrrolopyrimidine:

A suspension of 1 mMole of N7-((1'R,2'S,3'R,4'S)-2',3'-dihydroxy-4'-amino-cyclopentyl)-4-amino-5-iodo-pyrrolopyrimidine and 20 mMole of copper(I) cyanide is heated in a sealed robe at 130° C. for six hours, then cooled, and the reaction concentrated in vacuo. The residue is purified by flash chromatography to give the title product.

EXAMPLE 62

Synthesis of N7-((1'R,4'S)-trans-4'-(methanesulfonyl)oxy-2'-cyclopentenyl)-4-chloro-5-iodo-pyrrolopyrimidine:

To a suspension of 1 mMole of N7-((1'R,4'R)-trans-4'-hydroxy-2'-cyclopentyl)-4-chloro-pyrrolopyrimidine in dichloromethane/pyridine is added 1 mMole of triethylamine and 1 mMole of methanesulfonic anhydride at 0° C. The mixture is allowed to warm to 25° C. over 2 hours, concentrated in vacuo, and purified by flash chromatography.

EXAMPLE 64

Synthesis of N7-((1'R,4'S)-cis-4'-(diphenylphosphinyl)-2'-cyclopentenyl)-4-chloro-5-iodo-pyrrolopyrimidine:

To a solution of 1 mMole of N7-((1'R,4'S)-trans-4'-(methanesulfonyl)oxy-2'-cyclopentenyl)-4-chloro-5-iodo-pyrrolopyrimidine in tetrahydrofuran at -78° C. is added 1 mMole of lithium diphenylphosphide. The mixture is allowed to warm to 25° C. over 2 hours, concentrated in vacuo, and treated with 2 mMole of 30% hydrogen peroxide. The mixture is heated at reflux for 30 minutes, cooled, concentrated in vacuo, and purified by flash chromatography to give the title compound.

EXAMPLE 65

Synthesis of N7-((1'R,2'S,3'S,4'S)-2',3'-dihydroxy-4'-(diphenylphosphinyl)-cyclopentyl)-4-chloro-5-iodo-pyrrolopyrimidine:

To a solution of 1 mMole of N7-((1'R,4'S)-cis-4'-(diphenylphosphinyl)-2'-cyclopentenyl)-4-chloro-5-iodo-pyrrolopyrimidine in t-butanol/tetrahydrofuran at 10° C. is added 3 mMole of N-methylmorpholine-N-oxide and 0.2 mMole of solid osmium tetroxide. The mixture is allowed to warm to 25° C., stirred for 12 hours, then poured into ethyl acetate and washed with a mixture of 10% sodium thiosulfate and sodium phosphate buffer (pH 7). The organic phase is dried ($Na_2SO_4$), concentrated in vacuo, and purified by flash chromatography to give the title compound.

EXAMPLE 66

Synthesis of N7-((1'R,4'S)-cis-4'-(imidazol-1-yl)-2'-cyclopentenyl)-4-chloro-5-iodo-pyrrolopyrimidine:

To a solution of 1 mMole of N7-((1'R,4'S)-trans-4'-(methanesulfonyl)oxy-2'-cyclopentenyl)-4-chloro- 5-iodo-pyrrolopyrimidine in dichloromethane at 0° C. is added 1 mMole of imidazole. The mixture is allowed to warm to 25° C., stirred for 14 hours, concentrated in vacuo, and purified by flash chromatography.

EXAMPLE 67

Synthesis of N7-((1'R,2'S,3'S,4'S)-2',3'-dihydroxy-4'-(imidazol-1-yl)-cyclopentyl)-4-chloro-5-iodo-pyrrolopyrimidine:

To a solution of 1 mMole of N7-((1'R,4'S)-cis4'-N-imidazoyl-2'-cyclopentenyl)-4-chloro-5-iodo-pyrrolopyrimidine in t-butanol/tetrahydrofuran at 10° C. is added 3 mMole of N-methylmorpholine-N-oxide and 0.2 mMole of solid osmium tetroxide. The mixture is allowed to warm to 25° C., stirred for 12 hours, concentrated in vacuo, and purified by flash chromatography, eluting with acetone/hexane to give the title compound.

EXAMPLE 68

Synthesis of N7-((1'R,2'S,3'R,4'S)-2',3'-dihydroxy-4'-amino-cyclopentyl)-4-amino-5-methoxy-pyrrolopyrimidine:

A suspension of 1 mMole of N7-((1'R,2'S,3'R,4'S)-2',3'-dihydroxy-4'-amino-cyclopentyl)-4-amino-5-iodo-pyrrolopyrimidine, 10 mMole of sodium methoxide, and 0.1 mMole of copper(I) bromide in DMSO is heated in a sealed robe at 130° C. for six hours, cooled, and the reaction concentrated in vacuo. The residue is purified by flash chromatography to give the product

EXAMPLE 69

Synthesis of N7-(((1'R,2'S,3'R,4'S)-2',3'-dihydroxy)-4'-(bis-t-butoxycarbonylamino)-cyclopentyl)-4,5-bis-phenylacetylenyl-pyrrolopyrimidine:

A solution of 1 mMole of N7-((1'R,2'S,3'R,4'S)-2',3'-dihydroxy-4'-(bis-t-butoxycarbonylamino)-cyclopentyl)-4-chloro-5-iodo-pyrrolopyrimidine, 0.05 mMole of bis (triphenylphosphine) palladium(II)dichloride, 0.2 mMole of copper(I) iodide, 3 mMole of phenylacetylene, and 4 mL of triethylamine in acetonitrile is heated at 60° C. for six hours. Concentration in vacuo gives a syrup which is purified by flash chromatography to give the title compound.

EXAMPLE 70

Synthesis of N7-(((1'R,2'S,3'R,4'S)-2',3'-dihydroxy)-4'-amino-cyclopentyl)-4,5-bis-((2-phenyl)-ethyl))-pyrrolopyrimidine:

A suspension of 1 mMole of N7-(((1'R,2'S,3'R,4'S)-2',3'-dihydroxy)-4'-amino-cyclopentyl)-4,5-bis-phenylacetylenyl-pyrrolopyrimidine and 20 mg of 10% palladium on carbon in methanol is stirred under an atmosphere of hydrogen for two weeks. The mixture is filtered, concentrated in vacuo, and purified by flash chromatography to give the title product.

EXAMPLE 71

Synthesis of N7-((1'R,2'S,3'R,4'S)-2',3'-dihydroxy-4'-amino-cyclopentyl)-4-phenylmercapto-5-iodo-pyrrolopyrimidine:

To a solution of 1 mMole of thiophenol and 1 mMole of potassium hydride in dimethylformamide is added 1 mMole of N7-((1'R,2'S,3'R,4'S)-2',3'-dihydroxy-4'-(bis-t-butoxycarbonylamino)-cyclopentyl)-4-chloro-5-iodo-pyrrolopyrimidine. The solution is heated at 100° C. in a sealed vessel for 14 hours, then cooled. The solvent is removed by concentration in vacuo and the residue purified by flash chromatography to give a single product. This is dissolved in trifluoroacetic acid and after stirring for 10 minutes at 25° C., concentrated in vacuo and purified by flash chromatography to give the title compound.

EXAMPLE 72

Synthesis of N7-((1'R,2'S,3'R,4'S)-2',3'-dihydroxy-4'-(4"-chlorobenzyl)amino-cyclopentyl)-4-phenylmercapto-5-iodo-pyrrolopyrimidine: To a solution of 1 mMole of N7-((1'R,2'S,3'R,4'S)-2',3'-dihydroxy-4'-amino-cyclopentyl)-4-phenylmercapto-5-iodo-pyrrolopyrimidine and 1 mMoles of 4-chlorobenzaldehyde in dimethylformamide/toluene is added 1 gram of 4 Å molecular sieves. The mixture is heated at 50° C. with stirring for 12 hours, then cooled and concentrated in vacuo. This is treated with a 0.1M solution of sodium borohydride in methanol for 1 hour, then concentrated in vacuo and purified by flash chromatography to give the title compound.

EXAMPLE 73

Synthesis of N7-((1'R,2'S,3'S,4'S)-2',3'—O-(1-methylethylidene)-4'-(t-butyldimethylsilyloxy)-cyclopentyl)-4-chloro-pyrrolopyrimidine:

A mixture of 1 mMole of N7-((1'R,2'S,3'S,4'S)-2',3'-dihydroxy-4'-(t-butyldimethylsilyloxy)-cyclopentyl)-4-chloro-pyrrolopyrimidine, 3 mMole of 2,2-dimethoxypropane, and 0.02 mMole of 4-toluenesulfonic acid, in DMF is stirred at 25° C. for 24 hours. The reaction is then poured into ethyl acetate and washed with saturated sodium bicarbonate, dried over MgSO₄, and concentrated in vacuo. The residue is purified by flash chromatography.

EXAMPLE 74

Synthesis of N7-((1'R,2'S,3'R,4'S)-2',3'—O-(1-methylethylidene)-4'-(t-butyldimethylsilyloxy)-cyclopentyl)-4-chloro-5-bromo-pyrrolopyrimidine:

A mixture of 1 mMole of N7-((1'R,2'S,3'S,4'S)-2',3'—O-(1-methylethylidene)-4'-(t-butyldimethylsilyloxy)-cyclopentyl)-4-chloro-pyrrolopyrimidine, and 1 mMole of N-bromosuccinimide in dichloromethane is stirred at 25° C. for 72 hours. The reaction is then poured into ethyl acetate and washed with a mixture of 10% sodium thiosulfate and saturated sodium bicarbonate, dried over MgSO₄, and concentrated in vacuo. The residue is purified by flash chromatography.

EXAMPLE 75

Synthesis of N7-((1'R,2'S,3'S,4'S)-2',3'—O-(1-methylethylidene)-4'-hydroxy-cyclopentyl)-4-chloro-5-bromo-pyrrolopyrimidine:

A mixture of 1 mMole of N7-((1'R,2'S,3'S,4'S)-2',3'—O-(1-methylethylidene)-4'-(t-butyldimethylsilyloxy)-cyclopentyl)-4-chloro-5-bromo- pyrrolopyrimidine, and 2 mMole of tetra-(n-butyl)ammonium fluoride in tetrahydrofuran is stirred at 25° C. for 2 hours. The reaction is then concentrated in vacuo and the residue is purified by flash chromatography.

EXAMPLE 76

Synthesis of N7-((1'R,2'S,3'S)-2',3'—O-(1-methylethylidene)-4'-oxo-cyclopentyl)-4-chloro-5-bromo-pyrrolopyrimidine:

To a mixture of 2 mMole of oxalyl chloride in dichloromethane at −60° C. is added 4 mMole of dimethylsulfoxide over 2 minutes. After 5 minutes, a solution of 1 mMole of N7-((1'R,2'S,3'R,4'S)-2',3'—O-(1-methylethylidene)-4'-hydroxy-cyclopentyl)-4-chloro-5-bromo-pyrrolopyrimidine in dichloromethane is added over 2 minutes, and after 15 minutes, 1 mMole of di-isopropyl-ethylamine is added over 2 minutes. The reaction is stirred at −60° C. for 20 minutes, then warmed to room temperature and poured into ethyl acetate/hexane and washed with saturated sodium bicarbonate solution, dried over MgSO₄, concentrated in vacuo, and purified by flash chromatography.

EXAMPLE 77

Synthesis of N7-((1'R,2'S,3'R,4'S)-2',3'—O-(1-methylethylidene)-4'-(4"-dimethylaminobenzyl)amino-cyclopentyl)-4-chloro-5-bromo-pyrrolopyrimidine:

To a solution of 1 mMole of N7-((1'R,2'S,3'S)-2',3'—O-(1-methylethylidene)-4'-oxo-cyclopentyl)-4-chloro-5-bromo-pyrrolopyrimidine and 1 mMole of 4-(dimethylamino)benzyl amine in dimethylformamide and toluene is added 4 Å molecular sieves. The mixture is heated at 40° C. until imine formation is complete. The solution is cooled to 0° C., and 5 mMole of a 0.25M solution of sodium borohydride solution in ethanol is added with stirring. The reaction is maintained at 0° C. for one hour, quenched with water, then concentrated to a paste. This is diluted with dichloromethane, poured into dichloromethane and washed with sodium phosphate buffer (pH 7), dried over Na₂SO₄, and concentrated in vacuo. The residue is purified by flash chromatography to give the title product.

EXAMPLE 78

Synthesis of N7-((1'R,2'S,3'R,4'S)-2',3'-dihydroxy-4'-(4"-dimethylaminobenzyl)amino-cyclopentyl)-4-chloro-5-bromo-pyrrolopyrimidine:

A solution of 1 mMole of N7-((1'R,2'S,3'R,4'S)-2',3'—O-(1-methylethyldine)-4'-(4"-dimethylaminophenyl)-cyclopentyl)-4-chloro-5-bromo-pyrrolopyrimidine in 1N aqueous hydrochloric acid in tetrahydrofuran is stirred at 25° C. for two hours, then poured into dichloromethane and washed with sodium phosphate buffer (pH 7), dried over $Na_2SO_4$, and concentrated in vacuo. The residue is purified by flash chromatography to give the title product.

EXAMPLE 79

Synthesis of N7-((1'R,2'S,3'S,4'S)-2',3'—O-(1-methylethylidene)-4'-(t-butyldimethylsilyloxy)-cyclopentyl)-4-chloro-5-phenyl-pyrrolopyrimidine:

A mixture of 1 mMole of N7-((1'R,2'S,3'S,4'S)-2',3'—O-(1-methylethylidene)-4'-(t-butyldimethylsilyloxy) cyclopentyl)-4chloro-5-bromo-pyrrolopyrimidine, 1.2 mMole of phenyltrimethylstannane, and 0.05 mMole of tetrakis-triphenylphosphine palladium (0) in DMF was heated at 70° C. for 12 hours, then cooled, and concentrated in vacuo to a dark syrup. The residue was purified by flash chromatography to give the title product.

EXAMPLE 80

Synthesis of N7-((1'R,2'S,3'R,4'S)-2',3'—O-(1-methylethylidene)-4"-(t-butyldimethylsilyloxy)-cyclopentyl)-5-phenyl-pyrrolopyrimidine:

A mixture of 1 mMole of N7-((1'R,2'S,3'S,4'S)-2',3'—O-(1-methylethylidene)-4'-(t-butyldimethylsilyloxy)-cyclopentyl)-4-chloro-5-phenyl-pyrrolopyrimidine and 25 mg of 10% palladium on carbon in ethanol was hydrogenated under 3 atmospheres of hydrogen at 25° C. for one hour. The catalyst was removed by filtration, and the filtrate concentrated in vacuo. The residue was dissolved in tetrahydrofuran and treated with 1 mMole of tetra-(n-butyl) ammonium fluoride for 2 hours. The reaction was concentrated in vacuo and the residue was purified by flash chromatography to give the title product.

EXAMPLE 81

Synthesis of N7-((1'R,2'S,3'S)-2',3'—O-(1-methylethylidene)-4'-oxo-cyclopentyl)-5-phenyl-pyrrolopyrimidine:

To a mixture of 2 mMole of oxalyl chloride in dichloromethane at −60° C. is added 4 mMole of dimethylsulfoxide over 2 minutes. After 5 minutes, a solution of 1 mMole of N7-((1'R,2'S,3'R,4'S)-2',3'—O-(1-methylethylidene)-4'-(t-butyldimethylsilyloxy)-cyclopentyl)-5-phenyl-pyrrolopyrimidine in dichloromethane is added over 2 minutes, and after 15 minutes, 1 mMole of di-isopropylethylamine is added over 2 minutes. The reaction is stirred at −60° C. for 20 minutes, then warmed to room temperature and poured into ethyl acetate/hexane and washed with saturated sodium bicarbonate solution, dried over $MgSO_4$, concentrated in vacuo, and purified by flash chromatography.

EXAMPLE 82

Synthesis of N7-((1'R,2'S,3'R,4'R)-2',3'—O-(1-methylethylidene)-4'-(4"-dimethylaminobenzyl)amino-cyclopentyl)-5-phenyl-pyrrolopyrimidine:

To a solution of 1 mMole of N7-((1R,2'S,3'S)-2',3'—O-(1-methylethylidene)-4'-oxo-cyclopentyl)-5-phenyl-pyrrolopyrimidine and 1 mMole of 4-(dimethylamino) benzyl amino in tetrahydrofuran and toluene is added 4Å molecular sieves. The mixture is heated at 40° C. until imine formation is complete. The solution is cooled to 0° C., and 5 mMole of a 1M solution of methyl magnesium bromide in ether is added with stirring. The reaction is maintained at 0° C. for two hours, then quenched with water and concentrated to a paste. This is diluted with dichloromethane, then poured into dichloromethane and washed with sodium phosphate buffer (pH 7), dried over $Na_2SO_4$, and concentrated in vacuo. The residue is purified by flash chromatography to give the title product.

EXAMPLE 83

Synthesis of N7-((1'R,2'S,3'R,4'R)-2',3'-dihydroxy-4'-(4"-dimethylaminobenzyl)amino-cyclopentyl)-5-phenyl-pyrrolopyrimidine:

A solution of 1 mMole of N7-((1'R,2'S,3'R,4'R)-2',3'—O-(1-=methylethylidene)-4'-(4"-dimethylaminobenzyl)amino-cyclopentyl)-5-phenyl-pyrrolopyrimidine in 1N aqueous hydrochloric acid in tetrahydrofuran is stirred at 25° C. for two hours, then poured into dichloromethane and washed with sodium phosphate buffer (pH 7), dried over $Na_2SO_4$, and concentrated in vacuo. The residue is purified by flash chromatography to give the title product.

EXAMPLE 84

Synthesis of N7-((1'R,2'S,3'S)-2',3'-dihydroxy-4'-oxo-cyclopentyl)-5-phenyl-pyrrolopyrimidine:

A solution of 1 mMole of N7-((1'R,2'S,3'S)-2',3'—O-(1-methylethylidene)-4'-oxo-cyclopentyl)-5-phenyl-pyrrolopyrimidine in 1N aqueous hydrochloric acid in tetrahydrofuran is stirred at 25° C. for two hours, then poured into dichloromethane and washed with sodium phosphate buffer (pH 7), dried over $Na_2SO_4$, and concentrated in vacuo. The residue is purified by flash chromatography to give the title product.

EXAMPLE 85

Synthesis of N7-((1'R,2'S,3'S)-2',3'-dihydroxy-4'-oxo-cyclopentyl)-4-chloro-5-bromo-pyrrolopyrimidine:

A solution of 1 mMole of $N_7$-((1'R,2'S,3'S)-2',3'—O-(1-methylethylidene)-4'-oxo-cyclopentyl)-4-chloro-5-bromo-pyrrolopyrimidine in 1N aqueous hydrochloric acid in tetrahydrofuran is stirred at 25° C. for two hours, then poured into dichloromethane and washed with sodium phosphate buffer (pH 7), dried over $Na_2SO_4$, and concentrated in vacuo. The residue is purified by flash chromatography to give the title product.

EXAMPLE 86

Synthesis of N7-((1'R,4'S)-cis-4'-amino-2'-cyclopentenyl)-4-chloro-5-iodo-pyrrolopyrimidine:

A solution of 1 mMole of N7-((1'R,4'S)-cis-4'-(bis-t-butoxycarbonylamino)-2'-cyclopentenyl)-4-chloro-5-iodo-pyrrolopyrimidine in 5 mL of trifluoroacetic acid is stirred at 25° C. under nitrogen for 6 hours. The reaction is concentrated in vacuo, and the residue is then purified by flash chromatography, to give the title product.

EXAMPLE 87

Synthesis of N7-((1'R,4'S)-cis-4'-(t-butoxycarbonylamino)-cyclopentyl)-4-chloro-pyrrolopyrimidine:

To a solution of 1 mMole of N7-((1'R,4'S)-cis-4'-(bis-t-butoxycarbonylamino)-2'-cyclopentenyl)-4-chloro-5-iodo-pyrrolopyrimidine in methanol is added 50 mg of platinum oxide. The mixture is stirred at 25° C. under an atmosphere of hydrogen for 6 hours. The reaction is concentrated in vacuo, and the residue is then purified by flash chromatography, to give the title product.

EXAMPLE 88

Synthesis of N7-((1'R,4'S)-cis-4'-(t-butyoxycarbonylamino)-cyclopentyl)-4-chloro-5-iodo-pyrrolopyrimidine:

To a solution of 1 mMole of N7-((1'R,4'S)-cis-4'-(t-butyoxycarbonylamino)-2'-cyclopentyl)-4-chloro-pyrrolopyrimidine and 2 mMole of anyhydrous sodium carbonate in dichloromethane is added 1 mMole of a 1-M solution of iodine monochloride in dichloride. The mixture is stirred at 25° C. under an atmosphere of nitrogen for 16 hours. The reaction is concentrated in vacuo, and the residue is then purified by flash chromatography, to give the title product.

EXAMPLE 89

Synthesis of N7-((1'R,4'S)-cis-4'-amino-cyclopentyl)-4-chloro-5-iodo-pyrrolopyrimidine:

A solution of 1 mMole of N7-((1'R,4'S)-cis-4'-(t-butoxycarbonylamino)-cyclopentyl)-4-chloro-5-iodo-pyrrolopyrimidine in 5 mL of trifluoroacetic acid is stirred at 25° C. under nitrogen for 6 hours. The reaction is concentrated in vacuo, and the residue is then purified by flash chromatography, to give the title product.

EXAMPLE 90

Synthesis of N7-((1'R,4'S)-4'-(imidazol-1-yl)-cyclopentyl)-4-chloro-pyrrolopyrimidine:

To a solution of 1 mMole of N7-((1'R,4'S)-cis-4'-N-imidazoyl-2'-cyclopentenyl)-4-chloro-5-iodo-pyrrolopyrimidine in methanol is added 50 mg of platinum oxide. The mixture is stirred at 25° C. under an atmosphere of hydrogen for 6 hours. The reaction is concentrated in vacuo, and the residue is then purified by flash chromatography, to give the title product.

EXAMPLE 91

Synthesis of N7-((1'R,4'S)-4'-(imidazol-1-yl)-cyclopentyl)-4-chloro-5-iodo-pyrrolopyrimidine:

To a solution of 1 mMole of N7-((1'R,4'S)=4'-(imidazol-1-yl)-cyclopentyl)-4-chloro-pyrrolopyrimidine and 2 mMole of anyhydrous sodium carbonate in dichloromethane is added 1 mMole of a 1-M solution of iodine monochloride in dichloromethane. The mixture is stirred at 25° C. under an atmosphere of nitrogen for 16 hours. The reaction is concentrated in vacuo, and the residue is then purified by flash chromatography, to give the title product.

EXAMPLE 92

Synthesis of N7-((1R,2'R,4'S)-4'-(t-butyoxycarbonylamino)-2'-hydroxy-cyclopentyl)-4-chloro-5-iodo-pyrrolopyrimidine and N7-((1R,3'S,4'S)-4'-(t-butoxycarbonylamino)-3'-hydroxy-cyclopentyl)-4-chloro-5-iodo-pyrrolopyrimidine:

To a solution of 1 mMole of N7-((1'R,4'S)-cis-4'-(bis-t-butyoxycarbonylamino)-2'-cyclopentenyl)-4-chloro-5-iodo-pyrrolopyrimidine in tetrahydrofuran at 0° C. under nitrogen is added 3 mMoles of a 1-M solution of borane in tetrahydrofuran. The reaction is allowed to warm to 25° C. and stirred for 12 hours. The organoborane is oxidized by addition of 15 mMoles of N-methylmorpholine N-oxide. The reaction is monitored by thin layer chromatography until formation of the alcohol is complete. The reaction is concentrated in vacuo, and the residue is then purified by flash chromatography, to give the title products.

EXAMPLE 93

Synthesis of N7-((1'R,2'R,4'S)-4'-amino-2'-hydroxy-cyclopentyl)-4-chloro-5-iodo-pyrrolopyrimidine:

A solution of 1 mMole of N7-((1'R,2'R,4'S)-4'-(t-butoxycarbonylamino)-2'-hydroxy-cyclopentyl)-4-chloro-5-iodo-pyrrolopyrimidine in 5 mL of trifluoroacetic acid is stirred at 25° C. under nitrogen for 6 hours. The reaction is concentrated in vacuo, and the residue is then purified by flash chromatography, to give the title product.

EXAMPLE 94

Synthesis of N7-((1R,3'S,4'S)-4'-amino-3'-hydroxy-cyclopentyl)-4-chloro-5-iodo-pyrrolopyrimidine:

A solution of 1 mMole of N7-((1'R,3'S ,4'S)-4'-(t-butoxycarbonylamino)-3'-hydroxy-cyclopentyl)-4-chloro-5-iodo-pyrrolopyrimidine in 5 mL of trifluoroacetic acid is stirred at 25° C. under nitrogen for 6 hours. The reaction is concentrated in vacuo, and the residue is then purified by flash chromatography, to give the title product.

EXAMPLE 95

Synthesis of N7-((1'R,2'R,4'S)-4'-(imidazol-1-yl)-2'-hydroxy-cyclopentyl)-4-chloro-5-iodo-pyrrolopyrimidine and N7-((1'R,3'S,4'S)-4'-(imidazol-1-yl)-3'-hydroxy, cyclopentyl),4-chloro-5-iodo-pyrrolopyrimidine:

To a solution of 1 mMole of N7-((1'R,4'S)-cis-4'-(imidazol-1-yl)-2'-cyclopentenyl)-4-chloro-5-iodo-pyrrolopyrimidine in tetrahydrofuran at 0° C. under nitrogen is added 3 mMoles of a 1-M solution of borane in tetrahydrofuran. The reaction is allowed to warm to 25° C. and stirred for 12 hours. The organoborane is oxidized by addition of 15 mMoles of N-methylmorpholine N-oxide. The reaction is monitored by thin layer chromatography until formation of the alcohol is complete. The reaction is concentrated in vacuo, and the residue is then purified by flash chromatography, to give the title products.

What is claimed is:

1. A compound of the Formula I

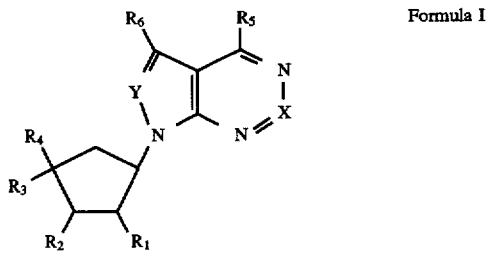

Formula I wherein

X is —$CR_7$ where $R_7$ is hydrogen, halogen, loweralkyl, loweralkoxy or —S— loweralkyl;

Y is —N or —CH;

$R_1$ and $R_2$ are each independently hydroxy, alkoxy, or acyloxy or $R_1$ and $R_2$ are both hydroxy protected with an individual hydroxy protecting group or with a single dihydroxy-protecting group or $R_1$ and $R_2$ are absent and there is a double bond between the carbon atoms to which $R_1$ and $R_2$ are attached;

$R_3$ is hydrogen, hydroxy, or alkoxy;

$R_4$ is a) hydrogen, b) amino, c) halogen, d) hydroxy, e) sufonamido, f) —$P(O)(OH)_2$, g) —P(O)—$R_8R_9$ wherein $R_8$ and $R_9$ are each independently hydrogen, hydroxy, loweralkyl, aryl, or arylalkyl, h) —$NHR_{10}$ wherein $R_{10}$ is hydrogen or an amino protecting group, i) —$NHC(O)NHR_{11}$ where $R_{11}$ is hydrogen or loweralkyl, or j) —A—$R_{12}$ wherein A is O, $S(O)_n$ or —$N(R_{13})$— wherein $R_{13}$ is hydrogen or loweralkyl, n is zero, one or two, and $R_{12}$ is hydrogen, loweralkyl, alkylsulfonyl, acyl, alkoxycarbonyl, aryl, heteroaryl, arylalkyl, arylsulfonyl, haloalkyl, heteroarylalkyl, heteroarylsulfonyl, aminoalkyl or heterocyclic or k) R4 is a ring N-member of a heteroaryl or heterocycle; or $R_3$ and $R_4$ taken together are =O, or taken together with the carbon atom to which they are attached, form a spirocyclic ring;

$R_5$ is hydrogen, loweralkyl, aryl, arylalkyl, heteroaryl, amino, alkylamino, alkoxy, acylamino, arylalkynyl, arylamino, arylmercapto, alkylmercapto, halogen, heterocyclic, hydrazino, —$NHC(O)NH_2$, or —$NR_{14}R_{15}$ wherein $R_{14}$ and $R_{15}$ are each independently hydrogen or an amino protecting group or —$NR_{14}R_{15}$ is a nitrogen containing heterocycle of 5 to 7 members; and $R_6$ is loweralkyl, cycloalkyl, alkenyl, alkynyl, alkoxy, alkoxycarbonyl, carboxy, aryl, heteroaryl, heteroarylalkyl, arylalkyl, arylalkenyl, arylalkynyl, cyano, halogen, heteroarylalkynyl, or —$C(O)NHR_{16}$ wherein $R_{16}$ is alkyl, aryl, or heterocyclic.

2. A compound according to claim 1 wherein X is —CH.

3. A compound according to claim 1 wherein $R_1$ and $R_2$ are —OH.

4. A compound according to claim 1 wherein $R_4$ is amino, hydroxyl, —$NHR_{10}$ or —$NR_{12}R_{13}$ where $R_{10}$, $R_{12}$ and $R_{13}$ are as defined in claim 1.

5. A compound according to claim 1 wherein $R_6$ is aryl, arylalkyl, arylalkenyl, arylalkynyl, or halogen.

6. A compound according to claim 1 wherein X is —CH; $R_1$ and $R_2$ are —OH; $R_4$ is amino, hydroxyl, —$NHR_{10}$ or —$NR_{12}R_{13}$ where $R_{10}$, $R_{12}$ and $R_{13}$ are as defined in claim 1, $R_5$ is amino, arylalkyl, arylalkynyl, arylamino or halogen and $R_6$ is aryl, arylalkyl, arylalkenyl, arylalkynyl, or halogen.

7. A compound according to claim 1 wherein $R_3$ is hydrogen and $R_4$ is hydroxy, or —$NHR_{10}$ wherein $R_{10}$ is hydrogen or an amino protecting group.

8. A compound according to claim 4, wherein $R_4$ is $NHR_{10}$ and $R_{10}$ is hydrogen, or an amino protecting group selected from the group consisting of carbamates, amides, N-alkyl groups, amino acetal groups, N-benzyl groups, imine groups, enamine groups, and N-heteroatom groups selected from the group consisting of nicotinyl, pyridazinyl, imidazole, and pyridinyl.

9. A compound according to claim 8 wherein $R_4$ is amino, methylamino, dimethylamino, carbamate, acylamino or heteroarylacylamino.

10. A compound according to claim 5 wherein $R_6$ is chloro, iodo, phenyl, 2-phenylethynyl or 2-phenylethyl.

11. A compound according to claim 1 wherein X is —CH; $R_1$ and $R_2$ are —OH; $R_3$ is hydrogen; $R_4$ is hydroxy, amino, or —$NHR_{10}$ wherein $R_{10}$ is hydrogen or an amino protecting group; $R_5$ is chloro, amino, phenylamino or 2-phenylethynyl; and $R_6$ is chloro, iodo, phenyl, 2-phenylethynyl or 2-phenylethyl.

12. A compound according to claim 1 having the Formula II

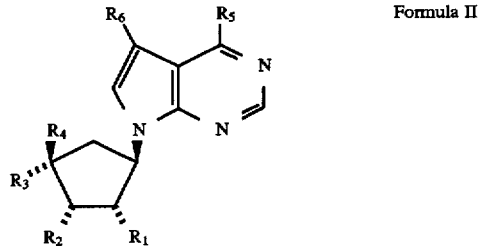

Formula II wherein $R_1$, $R_2$, $R_3$, $R_4$, $R_5$ and $R_6$ are as defined in claim 1.

13. A compound according to claim 1 having the Formula III, below

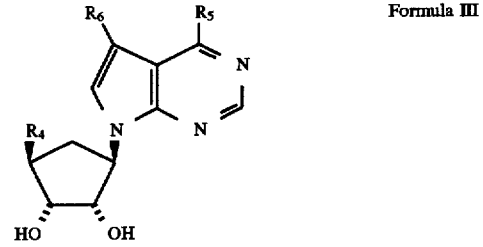

Formula III wherein $R_4$, $R_5$, and $R_6$ are as defined in claim 1.

14. A compound according to claim 13 wherein $R_4$ is amino, hydroxyl, —$NHR_{10}$ or —$NR_{12}R_{13}$ where $R_{10}$, $R_{12}$ and $R_{13}$ are as defined in claim 1.

15. A compound according to claim 13 wherein $R_6$ is aryl, arylalkyl, arylalkenyl, arylalkynyl, or halogen.

16. A compound according to claim 13 wherein $R_4$ is amino, hydroxyl, —$NHR_{10}$ or —$NR_{12}R_{13}$ where $R_{10}$, $R_{12}$ and $R_{13}$ are as defined in claim 1; $R_5$ is amino, arylalkyl, arylalkynyl, arylamino or halogen and $R_6$ is aryl, arylalkyl, arylalkenyl, arylalkynyl, or halogen.

17. A compound according to claim 13 wherein $R_4$ is amino, methylamino, dimethylamino, carbamate, acylamino or heteroarylacylamino.

18. A compound according to claim 13 wherein $R_6$ is chloro, iodo, phenyl, 2-phenylethyl or 2-phenylethynyl.

19. A compound according to claim 13 wherein $R_4$ is amino, methylamino, dimethylamino, carbamate, acylamino or heteroarylacylamino; $R_5$ is chloro, amino, phenylamino or 2-phenylethynyl; and $R_6$ is chloro, iodo, phenyl, 2-phenylethyl or 2-phenylethynyl.

20. A compound according to claim 19 wherein $R_4$ is hydroxyl and the values of $R_5$ and $R_6$ are:
a) $R_5$ is Cl and $R_6$ is Cl, I, phenyl, or 2-phenylethynyl;
b) $R_5$ is NH2 and $R_6$ is I, phenyl, 2-phenylethyl or 2-phenylethynyl;
c) $R_5$ is phenylamino and $R_6$ is I or phenyl;
d) $R_5$ is 2-phenylethynyl and $R_6$ is 2-phenylethynyl.

21. A compound according to claim 19 wherein:
a) $R_4$ is $NH_2$, $R_5$ is Cl or $NH_2$ and $R_6$ is I;
b) $R_4$ is $Boc_2N$, $R_5$ is Cl and $R_6$ is I;
c) $R_4$ is NHBoc, $R_5$ is $NH_2$ and $R_6$ is I;
d) $R_4$ is $CH_3NH$, $R_5$ is Cl and $R_6$ is $CH_3$;
e) $R_4$ is $(CH_3)_2N$, $R_5$ is Cl and $R_6$ is I; and
f) $R_4$ is nicotinamide, $R_5$ is Cl and $R_6$ is I.

22. A compound according to claim 1 having the Formula IV

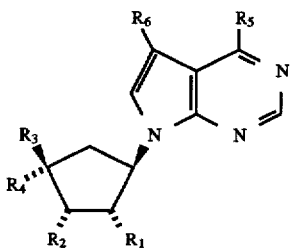

Formula IV wherein $R_1$, $R_2$, $R_3$, $R_4$, $R_5$ and $R_6$ are as defined in claim 1.

23. A compound according to claim 1 having the Formula V, below

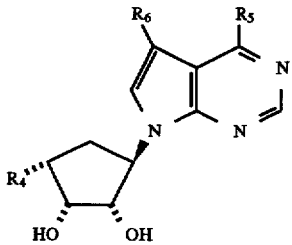

Formula V wherein $R_4$, $R_5$, and $R_6$ are as defined in claim 1.

24. A compound according to claim 23 wherein $R_4$ is amino, hydroxyl, $-NHR_{10}$ or $-NR_{12}R_{13}$ where $R_{10}$, $R_{12}$ and $R_{13}$ are as defined in claim 1.

25. A compound according to claim 23 wherein $R_6$ is aryl, arylalkyl, arylalkenyl, arylalkynyl, or halogen.

26. A compound according to claim 23 wherein $R_4$ is amino, hydroxyl, $-NHR_{10}$ or $-NR_{12}R_{13}$ where $R_{10}$, $R_{12}$ and $R_{13}$ are as defined in claim 1; $R_5$ is amino, arylalkyl, arylalkynyl, arylamino or halogen and $R_6$ is aryl, arylalkyl, arylalkenyl, arylalkynyl, or halogen.

27. A compound according to claim 23 wherein $R_4$ is amino, methylamino, dimethylamino, carbamate, acylamino or heteroarylacylamino.

28. A compound according to claim 23 wherein $R_6$ is chloro, iodo, phenyl, 2-phenylethyl or 2-phenylethynyl.

29. A compound according to claim 23 wherein $R_4$ is amino, methylamino, dimethylamino, carbamate, acylamino or heteroarylacylamino; $R_5$ is chloro, amino, phenylamino or 2-phenylethynyl; and $R_6$ is chloro, iodo, phenyl, 2-phenylethyl or 2-phenylethynyl.

30. A pharmaceutical composition comprising a therapeutically effective amount of a compound according to claim 1 in combination with a pharmaceutically acceptable carrier.

31. A method for inhibiting adenosine kinase comprising exposing adenosine kinase to an effective inhibiting amount of a compound of claim 1.

32. A method of treating cerebral ischemia, epilepsy, nociception, inflammation anal sepsis in a subject in need of such treatment, comprising administering to the subject a therapeutically effective amount of a compound according to claim 1.

* * * * *

UNITED STATES PATENT AND TRADEMARK OFFICE
CERTIFICATE OF CORRECTION

PATENT NO. : 5,665,721
DATED : September 9, 1997
INVENTOR(S) : Bhagwat et al.

It is certified that error appears in the above-identified patent and that said Letters Patent is hereby corrected as shown below:

Column 52, line 37, change "anal" to --and--.

Signed and Sealed this

Third Day of March, 1998

Attest:

BRUCE LEHMAN

Attesting Officer

Commissioner of Patents and Trademarks